US012429444B2

(12) United States Patent
Futagawa et al.

(10) Patent No.: US 12,429,444 B2
(45) Date of Patent: Sep. 30, 2025

(54) MOISTURE SENSOR

(71) Applicant: NATIONAL UNIVERSITY CORPORATION SHIZUOKA UNIVERSITY, Shizuoka (JP)

(72) Inventors: Masato Futagawa, Hamamatsu (JP); Kisho Sakamoto, Hamamatsu (JP)

(73) Assignee: NATIONAL UNIVERSITY CORPORATION SHIZUOKA UNIVERSITY (JP)

( * ) Notice: Subject to any disclaimer, the term of this patent is extended or adjusted under 35 U.S.C. 154(b) by 372 days.

(21) Appl. No.: 18/248,815

(22) PCT Filed: Oct. 14, 2021

(86) PCT No.: PCT/JP2021/038081
§ 371 (c)(1),
(2) Date: Apr. 12, 2023

(87) PCT Pub. No.: WO2022/080456
PCT Pub. Date: Apr. 21, 2022

(65) Prior Publication Data
US 2023/0417693 A1 Dec. 28, 2023

(30) Foreign Application Priority Data
Oct. 15, 2020 (JP) ................. 2020-173878

(51) Int. Cl.
G01N 25/56 (2006.01)
A01G 25/16 (2006.01)
H10N 10/17 (2023.01)

(52) U.S. Cl.
CPC .......... G01N 25/56 (2013.01); A01G 25/167 (2013.01); H10N 10/17 (2023.02)

(58) Field of Classification Search
CPC ...... G01N 25/56; G01N 25/58; A01G 25/167; H01N 10/17
See application file for complete search history.

(56) References Cited

U.S. PATENT DOCUMENTS 5,792,938 A * 8/1998 Gokhfeld ............. G01N 27/124
73/29.02

FOREIGN PATENT DOCUMENTS

CN 111562284 A 8/2020
DE 4331016 A1 3/1995
(Continued)

OTHER PUBLICATIONS

English translation of the International Search Report mailed Dec. 21, 2021, issued in corresponding PCT International Application No. PCT/JP2021/038081.
(Continued)

Primary Examiner — Paul M. West
(74) Attorney, Agent, or Firm — OSTROLENK FABER LLP

(57) ABSTRACT

The soil moisture sensor includes a thermoelectric element disposed in the soil, a first temperature information acquisition unit acquiring a first temperature information that indicates a temporal change in temperature of the soil due to an operation of the thermoelectric element, a second temperature information acquisition unit acquiring a second temperature information that indicates a temporal change in temperature of the soil due to the operation of the thermoelectric element, and an arithmetic device obtaining moisture information on the basis of the temperature information. The arithmetic device includes a gradient information acquisition unit acquiring a temperature change amount per unit time by utilizing the first temperature information and the second temperature information, and a conversion unit converting the temperature change amount into the moisture
(Continued)

content by utilizing conversion information indicating a relationship between the temperature change amount and the moisture content.

15 Claims, 19 Drawing Sheets

(56) References Cited

FOREIGN PATENT DOCUMENTS

| | | |
|---|---|---|
| JP | H11-281601 A | 10/1999 |
| JP | H11-304738 A | 11/1999 |
| JP | H11-304739 A | 11/1999 |
| JP | 2002-048742 A | 2/2002 |
| JP | 2005-283506 A | 10/2005 |
| JP | 2006-194821 A | 7/2006 |
| JP | 2009-097919 A | 5/2009 |

OTHER PUBLICATIONS

English translation of the International Preliminary Report on Patentability (IPRP) (Chapter 1 or II of the PCT Treaty) mailed Apr. 20, 2023 with a copy of Notification from the International Bureau (Form PCT/IB/338) in corresponding PCT International Application No. PCT/JP2021/038081.

Pedro Carvalhaes Dias et al.: "Proposal of a Novel Heat Dissipation Soil Moisture Sensor", IEEE Recent Researches in Circuits, Systems and Signal Processing, Jul. 2011, pp. 124-127.

Partial supplementary European Search Report dated Sep. 30, 2024, issued in corresponding European Patent Application No. 21880191.8.

Extended European Search Report dated Jan. 3, 2025, issued in corresponding European Patent Application No. 21880191.8.

\* cited by examiner

Fig.10
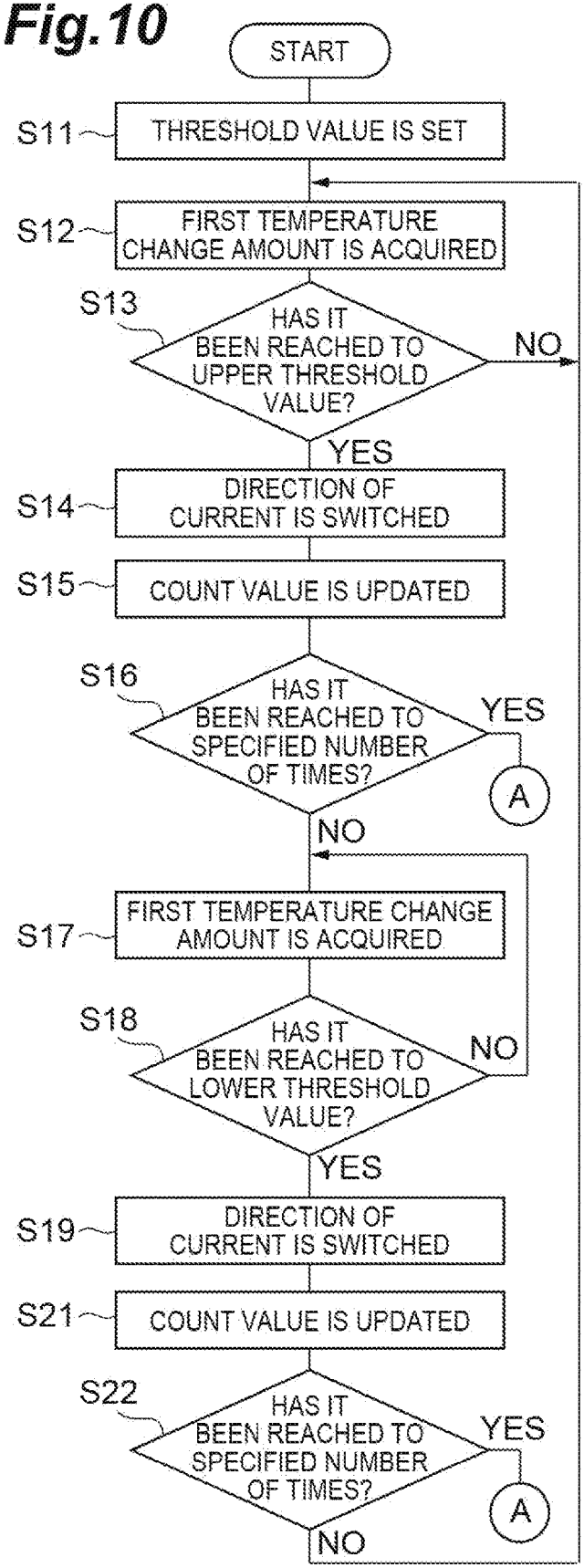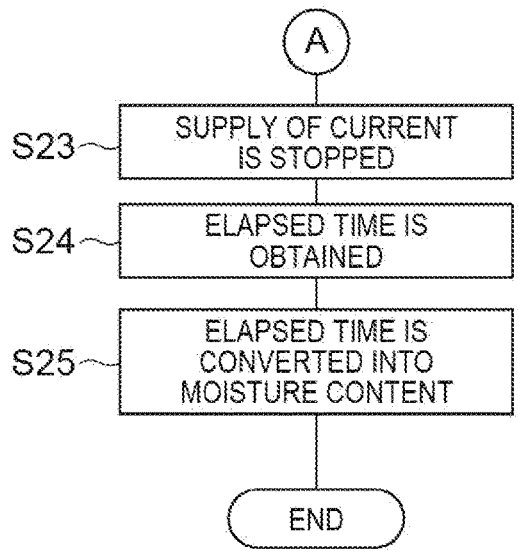

Fig.14
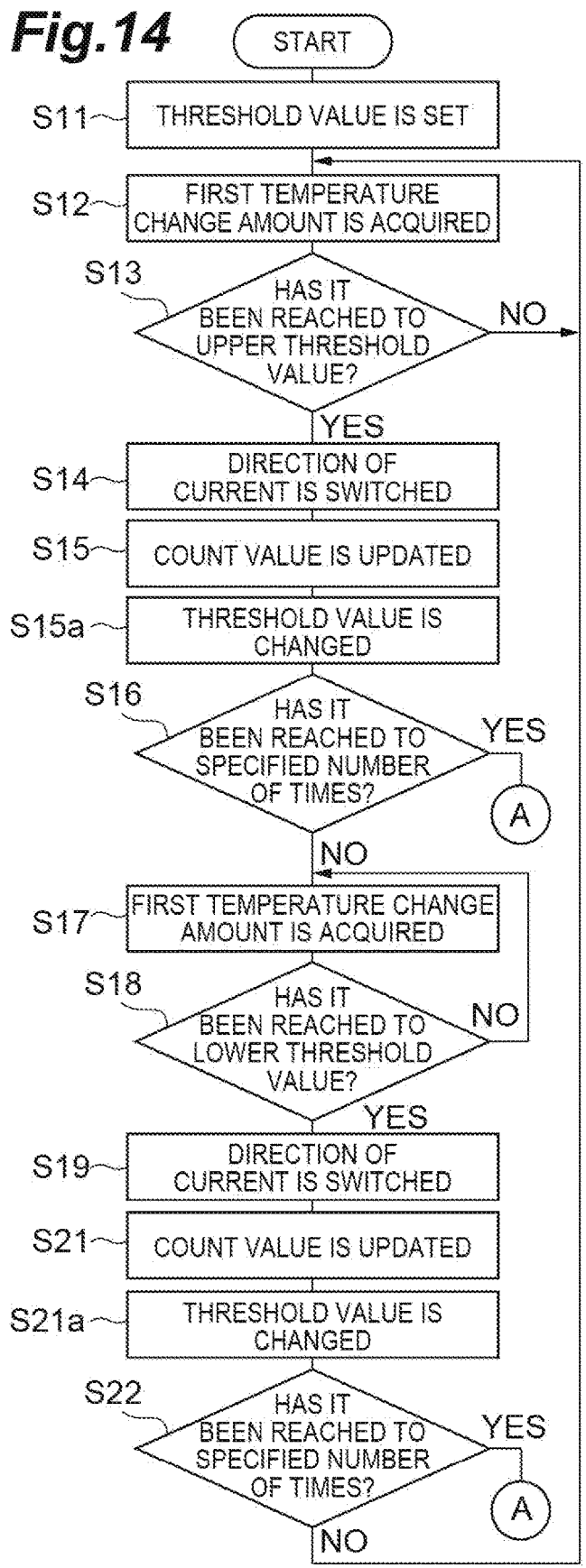
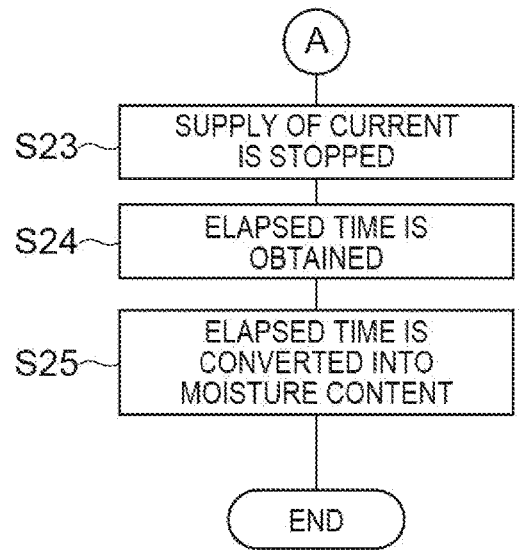

Fig.15
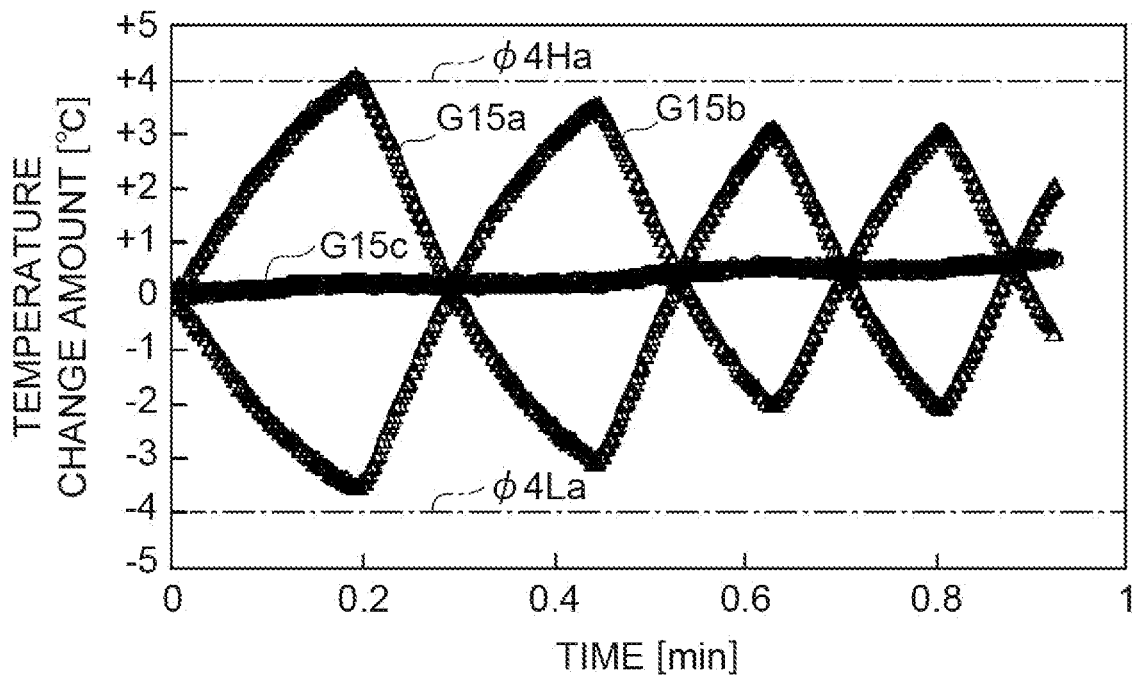
(a)
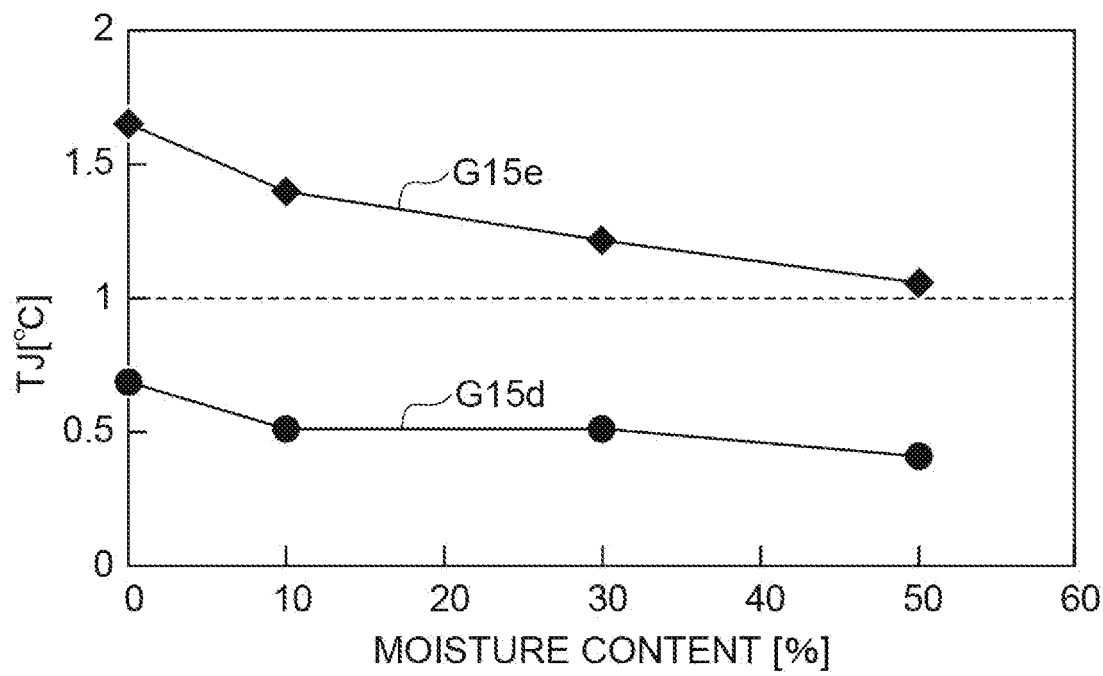
(b)

Fig.16
(a)
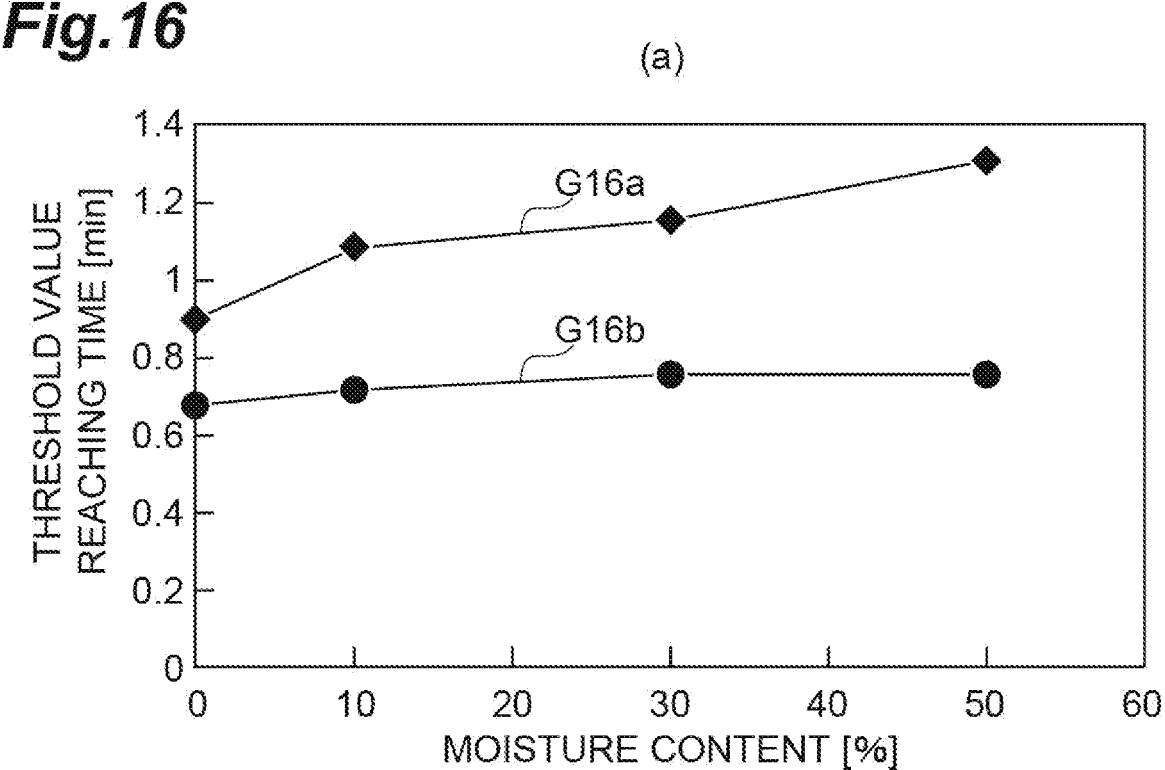
(b)
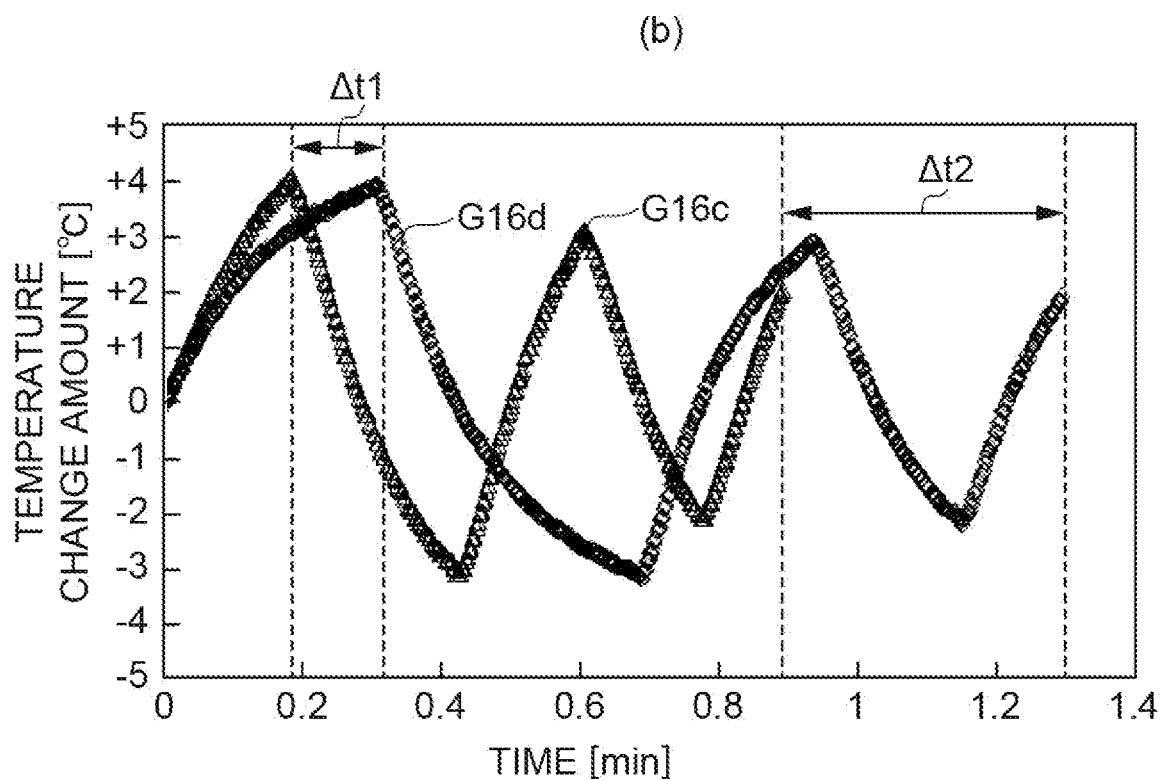

*Fig.19*
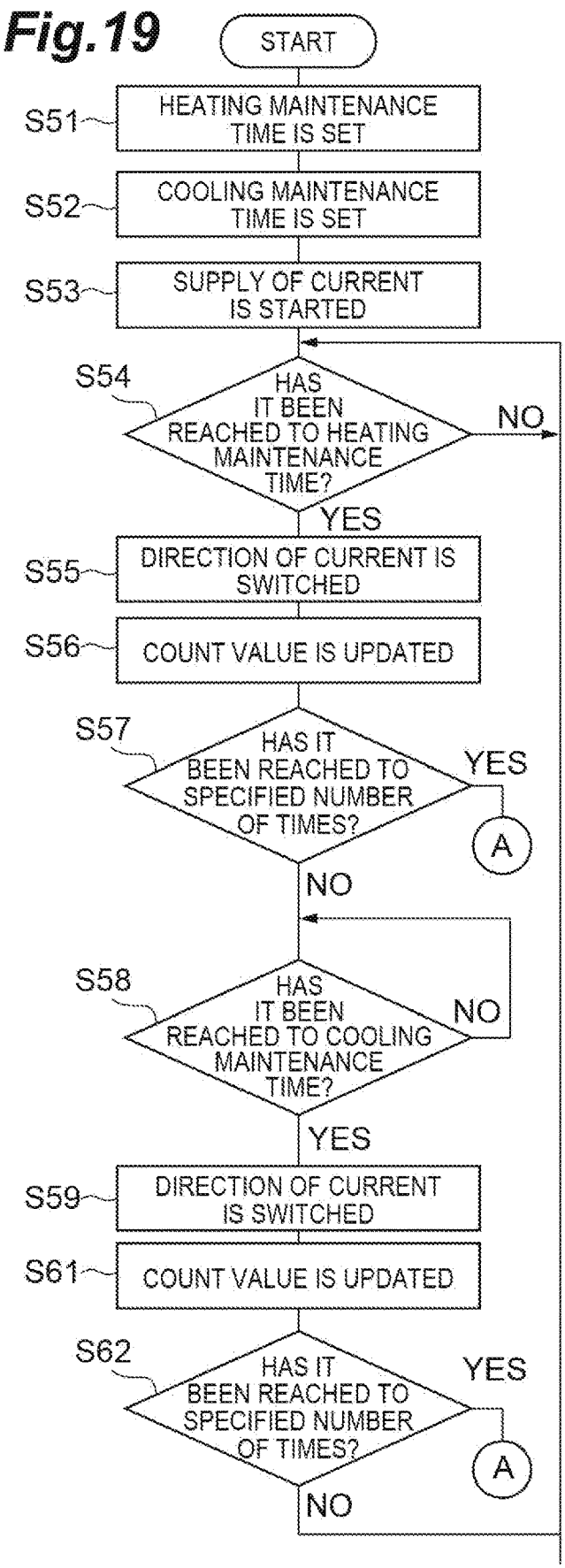
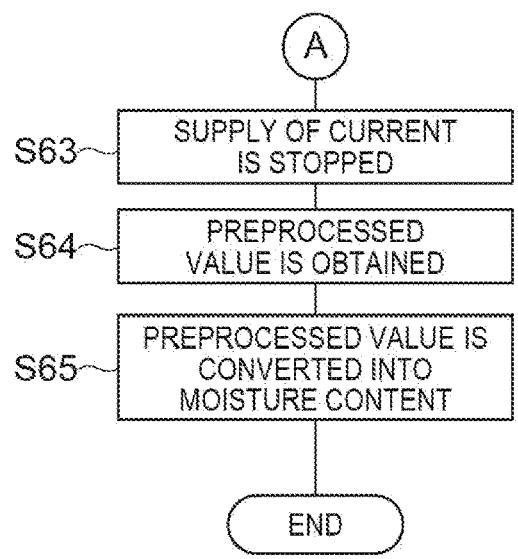

MOISTURE SENSOR

CROSS-REFERENCE TO RELATED APPLICATIONS

The present application is a 35 U.S.C. §§ 371 national stage application of International Application No. PCT/JP2021/038081, filed Oct. 14, 2021, which claims priority to Japanese Patent Application No. 2020-173878, filed Oct. 15, 2020, the contents of which are incorporated herein by reference.

TECHNICAL FIELD

The present invention relates to a moisture sensor which obtains information on moisture contained in a measurement subject.

BACKGROUND ART

In the field of agriculture, decrease in the number of farmers and the aging of farmers are regarded as problems. Precision agriculture has been studied as a technology for growing high-quality crops without relying on experience of farmers. In precision agriculture, various sensors are used to measure a condition of soil in which crops are grown. When a result of measuring the soil condition is utilized, it becomes possible to obtain an optimum moisture content and soil composition for crops.

Non-Patent Literature 1 discloses a technology related to a soil moisture sensor. In the soil moisture sensor of Non-Patent Literature 1, a probe for measurement is disposed in a soil. The probe of Non-Patent Literature 1 includes a case formed of a porous material and a transistor accommodated in the case.

CITATION LIST

Non-Patent Literature

[Non-Patent Literature 1] Pedro Carvalhaes Dias et al., "Proposal of a Novel Heat Dissipation Soil Moisture Sensor," IEEE Recent Researches in Circuits, Systems and Signal Processing, July 2011, pp. 124-127.

SUMMARY OF INVENTION

Technical Problem

As indicators representing soil conditions, for example, an ion concentration, a moisture content, pH, a temperature, and the like can be mentioned. For example, a TDR method and a capacitance method have been studied as technologies for obtaining a moisture content. The TDR method utilizes reflection of electromagnetic waves. The capacitance method utilizes electrical impedance and a relative dielectric constant. In the TDR method and the capacitance method, a moisture content is obtained by utilizing a relative dielectric constant based on a combined capacitance of a measurement object. The relative dielectric constant is affected by a concentration of ions contained in water. Therefore, even if the moisture content is the same, measured values may vary due to an influence of the ion concentration.

An objective of the present invention is to provide a moisture sensor capable of obtaining stable measurement results.

Solution to Problem

One embodiment of the present invention is a moisture sensor which obtains moisture information on moisture contained in a measurement object. The moisture sensor includes a temperature control unit disposed in the measurement object and being able to change a temperature of the measurement object, a temperature information acquisition unit acquiring temperature information indicating a temporal change of the temperature of the measurement object due to an operation of the temperature control unit, and an arithmetic unit obtaining the moisture information on the basis of the temperature information. The arithmetic unit includes a gradient information acquisition unit acquiring a temperature change amount per unit time by utilizing the temperature information, and a conversion unit converting the temperature change amount into the moisture information by utilizing conversion information indicating a relationship between the temperature change amount and the moisture information.

The moisture sensor obtains a temperature change amount when it performs an operation of changing a temperature of the measurement object. The temperature change amount is related to information on moisture contained in the measurement object. The temperature change amount is based on specific heat of the measurement object. The specific heat of the measurement object is a physical quantity. The specific heat, which is a physical quantity, is less susceptible to a disturbance. Therefore, stable measurement results can be obtained by obtaining information on the moisture by utilizing the temperature change amount caused by specific heat.

The temperature control unit of the moisture sensor of one embodiment may be a thermoelectric element which converts electrical energy into thermal energy. The thermoelectric element can switch between heating and cooling by switching between positive and negative polarities of a voltage. According to this characteristic, the temperature of the measurement object can be kept within a predetermined range.

The thermoelectric element of the moisture sensor of one embodiment may include a first heat input/output surface and a second heat input/output surface which are in contact with the measurement object and configured to provide heat to the measurement object and dissipate heat from the measurement object. The temperature information acquisition unit may include a first temperature measurement unit attached to the first heat input/output surface, and a second temperature measurement unit attached to the second heat input/output surface. According to this configuration, it is possible to obtain the temperature change amount based on two different aspects. As a result, more stable measurement results can be obtained.

In the moisture sensor of one embodiment, the thermoelectric element may be able to perform an operation of providing heat to the measurement object from one of the first heat input/output surface and the second heat input/output surface, and dissipating heat from the measurement object by the other of the first heat input/output surface and the second heat input/output surface. The gradient information acquisition unit may acquire a first temperature change amount by utilizing first temperature information obtained from the first temperature measurement unit and may acquire a second temperature change amount by utilizing second temperature information obtained from the second temperature measurement unit. The conversion unit may obtain the moisture information by utilizing the conversion information, the first temperature change amount, and the second temperature change amount. According to this configuration, it is possible to improve an accuracy of measurement results.

In the moisture sensor of one embodiment, the gradient information acquisition unit may acquire the temperature change amount using a difference between a first temperature and a second temperature during a transient period in a change of the temperature of the measurement object over time.

In the moisture sensor of one embodiment, the temperature information acquisition unit may be disposed to be in contact with the measurement object.

A moisture sensor, which is another embodiment of the present invention, obtains moisture information on moisture contained in a measurement object. The moisture sensor of another embodiment includes a thermoelectric element disposed in the measurement object and being able to change a temperature of the measurement object, a power supply unit supplying a current to the thermoelectric element and being able to switch a direction of the current supplied to the thermoelectric element, a temperature information acquisition unit acquiring the temperature of the measurement object, and a moisture content acquisition unit controlling a direction of the current supplied to the thermoelectric element from the power supply unit and acquiring the moisture information by utilizing the temperature acquired by the temperature information acquisition unit.

In the moisture sensor of another embodiment, the moisture content acquisition unit may include a switching control unit which controls a direction of the current supplied to the thermoelectric element from the power supply unit by utilizing the temperature of the measurement object.

In the moisture sensor of another embodiment, the switching control unit may perform a switching operation of switching a direction of the current supplied to the thermoelectric element from the power supply unit when the temperature of the measurement object has reached at least one predetermined threshold value.

In the moisture sensor of another embodiment, the switching control unit may perform the switching operation N times (N is an integer of 1 or more). The moisture content acquisition unit may acquire the moisture information using an elapsed time required for the switching operation of N times.

In the moisture sensor of another embodiment, the switching control unit may control a direction of the current supplied to the thermoelectric element from the power supply unit by utilizing one predetermined threshold value.

In the moisture sensor of another embodiment, the switching control unit may control a direction of the current supplied to the thermoelectric element from the power supply unit by utilizing a plurality of predetermined threshold values different from each other.

In the moisture sensor of another embodiment, an absolute value of the threshold value utilized when the measurement object is cooled may be smaller than an absolute value of the threshold value utilized when the measurement object is heated.

In the moisture sensor of another embodiment, the thermoelectric element may include a first heat input/output surface and a second heat input/output surface which are in contact with the measurement object and configured to provide heat to the measurement object and dissipate heat from the measurement object. The temperature information acquisition unit may include a first temperature measurement unit attached to the first heat input/output surface. The plurality of threshold values may include one or more upper threshold values higher than the temperature of the measurement object before a start of measurement and one or more lower threshold values lower than the temperature of the measurement object before the start of measurement. The switching control unit may switch a direction of the current when a temperature acquired by the first temperature measurement unit has reached the upper threshold value or the lower threshold value.

In the moisture sensor of another embodiment, the thermoelectric element may include a first heat input/output surface and a second heat input/output surface which are in contact with the measurement object and configured to provide heat to the measurement object and dissipate heat from the measurement object. The temperature information acquisition unit may include a first temperature measurement unit attached to the first heat input/output surface, and a second temperature measurement unit attached to the second heat input/output surface. The plurality of threshold values may include one or more upper threshold values higher than the temperature of the measurement object before a start of measurement. The switching control unit may switch a direction of the current when a temperature acquired by the first temperature measurement unit has reached the upper threshold value or when a temperature acquired by the second temperature measurement unit has reached the upper threshold value.

In the moisture sensor of another embodiment, the temperature information acquisition unit may acquire the temperature of the measurement object before the start of measurement as a reference temperature. The switching control unit may stop supply of a current from the power supply unit to the thermoelectric element when the temperature acquired by the first temperature measurement unit is determined to have reached the reference temperature during supply of the current from the power supply unit to the thermoelectric element.

In the moisture sensor of another embodiment, the thermoelectric element may include a first heat input/output surface and a second heat input/output surface which are in contact with the measurement object and configured to provide heat to the measurement object and dissipate heat from the measurement object. The temperature information acquisition unit may include a first temperature measurement unit attached to the first heat input/output surface, and a second temperature measurement unit attached to the second heat input/output surface on a side opposite to the first heat input/output surface. The plurality of threshold values may include one or more lower threshold values lower than the temperature of the measurement object before the start of measurement. The switching control unit may switch a direction of the current when a temperature acquired by the first temperature measurement unit has reached the lower threshold value or when a temperature acquired by the second temperature measurement unit has reached the lower threshold value.

In the moisture sensor of another embodiment, the switching control unit may stop supply of the current from the power supply unit to the thermoelectric element when the temperature acquired by the first temperature measurement unit and the temperature acquired by the second temperature measurement unit are determined to coincide with each other.

In the moisture sensor of another embodiment, the moisture content acquisition unit may include a switching control unit which controls a direction of the current supplied to the thermoelectric element from the power supply unit each time a predetermined switching time elapses.

In the moisture sensor of another embodiment, the moisture content acquisition unit may acquire the moisture information by utilizing at least one extreme value of the temperature of the measurement object.

In the moisture sensor of another embodiment, the thermoelectric element may include a first heat input/output surface and a second heat input/output surface which are in contact with the measurement object and configured to provide heat to the measurement object and dissipate heat from the measurement object. The temperature information acquisition unit may include a first temperature measurement unit attached to the first heat input/output surface, and a second temperature measurement unit attached to the second heat input/output surface. The switching control unit may stop supply of the current from the power supply unit to the thermoelectric element when a temperature acquired by the first temperature measurement unit and a temperature acquired by the second temperature measurement unit are determined to coincide with each other.

Advantageous Effects of Invention

According to the present invention, a moisture sensor capable of obtaining stable measurement results is provided.

BRIEF DESCRIPTION OF DRAWINGS

FIG. 10 is a flowchart showing an operation of the moisture sensor shown in FIG. 7.

FIG. 14 is a flowchart showing an operation of the moisture sensor shown in FIG. 12.

FIG. 15(a) is a graph showing a result of experimental example 1. FIG. 15(b) is a graph showing a result of experimental example 2.

FIG. 16(a) is a graph showing a result of experimental example 3. FIG. 16(b) is a graph showing a result of experimental example 4.

FIG. 19 is a flowchart showing an operation of the moisture sensor shown in FIG. 17.

DESCRIPTION OF EMBODIMENTS

Hereinafter, embodiments for implementing the present invention will be described in detail with reference to the accompanying drawings. In the description of the drawings, the same elements will be denoted by the same reference signs, and duplicate description thereof will be omitted.

Figure 1:
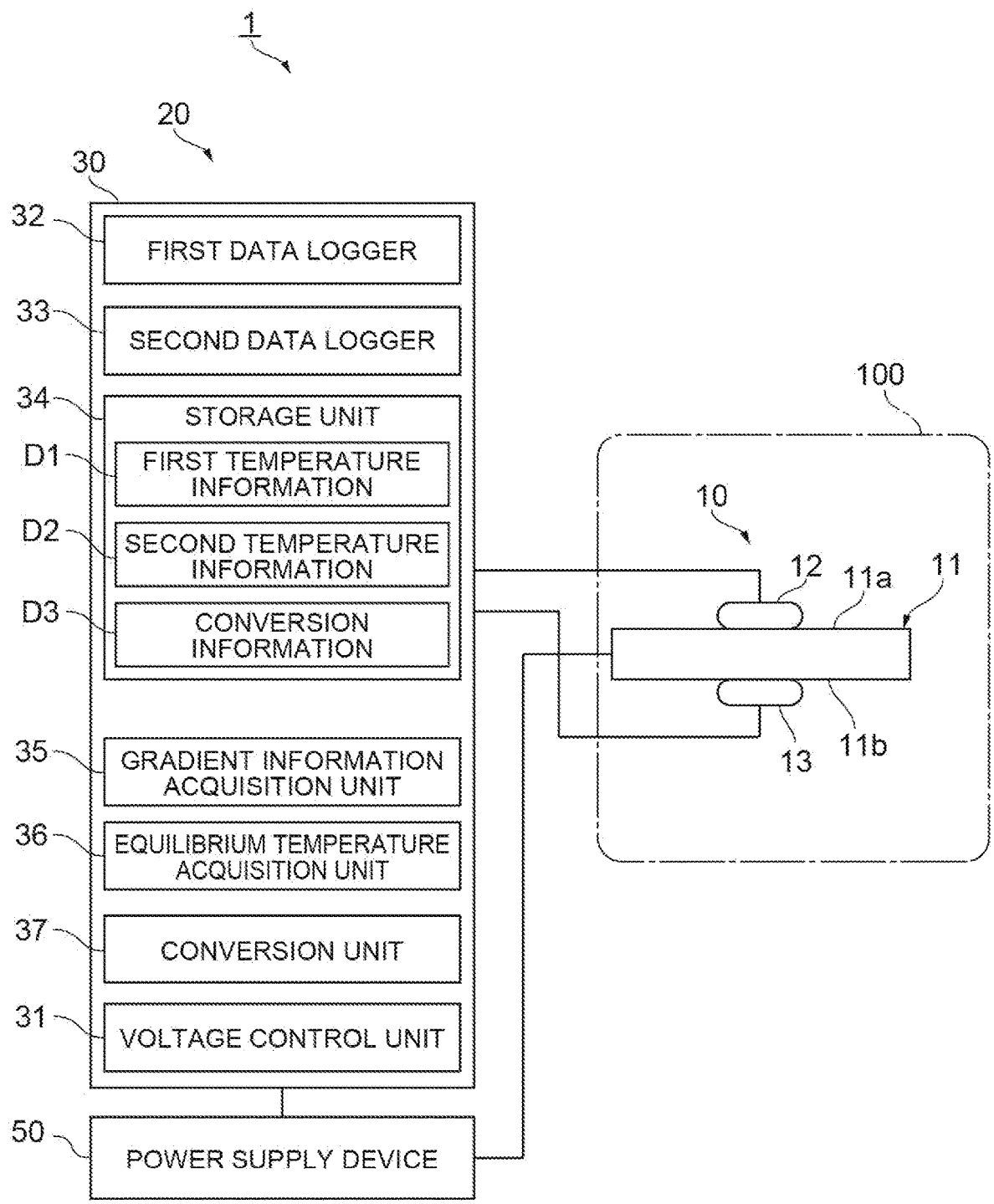
FIG. 1 is a diagram schematically showing a configuration of a moisture sensor of a first embodiment.

As shown in FIG. 1, a moisture sensor obtains a moisture content contained in a measurement object. In a first embodiment, a soil 100 is exemplified as the measurement object. In the following description, the moisture sensor is referred to as a soil moisture sensor 1. The soil moisture sensor 1 includes a sensor unit 10 and a control unit 20. The sensor unit 10 is embedded in the soil 100. The control unit 20 is disposed outside the soil 100. The sensor unit 10 is electrically connected to the control unit 20 by a cable or the like.

The sensor unit 10 includes a thermoelectric element 11 (temperature control unit), a first temperature measurement unit 12, and a second temperature measurement unit 13. An example of the thermoelectric element 11 is a Peltier element. The thermoelectric element 11 is electrically connected to the control unit 20 via a cable. The thermoelectric element 11 receives a predetermined voltage from the control unit 20. When a voltage is applied to the thermoelectric element 11, a temperature of one surface rises. When the voltage is applied to the thermoelectric element 11, a temperature of the other surface decreases. The two surfaces that operate differently from each other as described above are referred to as a first heat input/output surface 11a and a second heat input/output surface 11b.

The thermoelectric element 11 has the first heat input/output surface 11a and the second heat input/output surface 11b. When the thermoelectric element 11 has a flat plate shape, the first heat input/output surface 11a is a main surface. The second heat input/output surface 11b is a back surface. A portion of the soil 100 with which the first heat input/output surface 11a is in contact is different from another portion of the soil 100 with which the second heat input/output surface 11b is in contact.

The thermoelectric element 11 can be switched between heating and cooling according to a polarity of an input voltage. According to the thermoelectric element 11, when the soil 100 is heated and/or cooled for measurement, a temperature of the soil 100 changes from an initial state. Therefore, a voltage having a polarity opposite to that at the time of measurement is applied to the thermoelectric element 11. A portion of the heated soil 100 is cooled. Another portion of the cooled soil 100 is heated. As a result, the temperature in the initial state can be quickly restored. An influence of the temperature of the soil 100 on crops can be suppressed.

In other words, the thermoelectric element 11 can alternately switch between a heating part and a cooling part. In order to exhibit a function of alternately switching between the heating part and the cooling part, a positive current and a negative current are alternately applied to the thermoelectric element 11 for each measurement. As a result, a temperature of a measurement area rising greatly can be suppressed. Further, a temperature of the measurement area decreasing greatly can also be suppressed. Moreover, a cooling time of a probe after measurement is unnecessary. As a result, continuous measurement is made possible. Further, a moisture content can be measured without being affected by an ion concentration in water.

The first temperature measurement unit 12 is fixed to the first heat input/output surface 11a. The first temperature measurement unit 12 obtains a temperature of the first heat input/output surface 11a. Therefore, the first temperature measurement unit 12 does not measure only the temperature of the soil 100 alone. The first temperature measurement unit 12 measures a temperature of a system including the thermoelectric element 11 and the soil 100 in contact with the thermoelectric element 11. The temperature of the first temperature measurement unit 12 includes effects of thermal properties such as a thermal capacity and thermal conductivity of the thermoelectric element 11 and, thermal properties of the soil 100. For example, as a factor affected by the thermal properties of the thermoelectric element 11, a time difference (time lag) from the start of application of electricity to the start of temperature rise can be exemplified. The soil 100 is in contact with the first heat input/output surface 11a. Further, the first temperature measurement unit 12 is also provided on the first heat input/output surface 11a. With such a configuration, a treatment of eliminating the influence caused by the thermal properties of the thermoelectric element 11 is possible.

The first temperature measurement unit 12 is electrically connected to the control unit 20 via a cable. The first temperature measurement unit 12 outputs a signal on a temperature to the control unit 20. The second temperature measurement unit 13 is fixed to the second heat input/output surface 11b. The second temperature measurement unit 13 obtains a temperature of the second heat input/output surface 11b. The second temperature measurement unit 13 is electrically connected to the control unit 20 via a cable. The second temperature measurement unit 13 outputs a signal on a temperature to the control unit 20.

The control unit 20 operates the sensor unit 10. The control unit 20 obtains a moisture content of the soil 100 by processing a signal transmitted from the sensor unit 10. The control unit 20 includes an arithmetic device 30 (arithmetic unit) and a power supply device 50 (power supply unit).

The arithmetic device 30 outputs a control signal to the power supply device 50. The power supply device 50 includes a DC power supply 50a (see FIG. 4). The power supply device 50 outputs a voltage according to the control signal to the thermoelectric element 11. As a result, the thermoelectric element 11 operates. The power supply device 50 outputs a DC voltage to the thermoelectric element 11. The power supply device 50 can adjust a level of the voltage according to the control signal. The power supply device 50 can set a positive or negative polarity of the voltage according to the control signal. When positive and negative polarities of the voltage are reversed, for example, the first heat input/output surface, which has been a heating surface, can be switched to a cooling surface.

The arithmetic device 30 receives a signal on a temperature from the first temperature measurement unit 12 and the second temperature measurement unit 13. The signal on a temperature may be, for example, a voltage signal. The arithmetic device 30 obtains a moisture content of the soil 100 using the voltage signal.

Hereinafter, processing of obtaining a moisture content performed by the arithmetic device 30 will be described.

Figure 2:
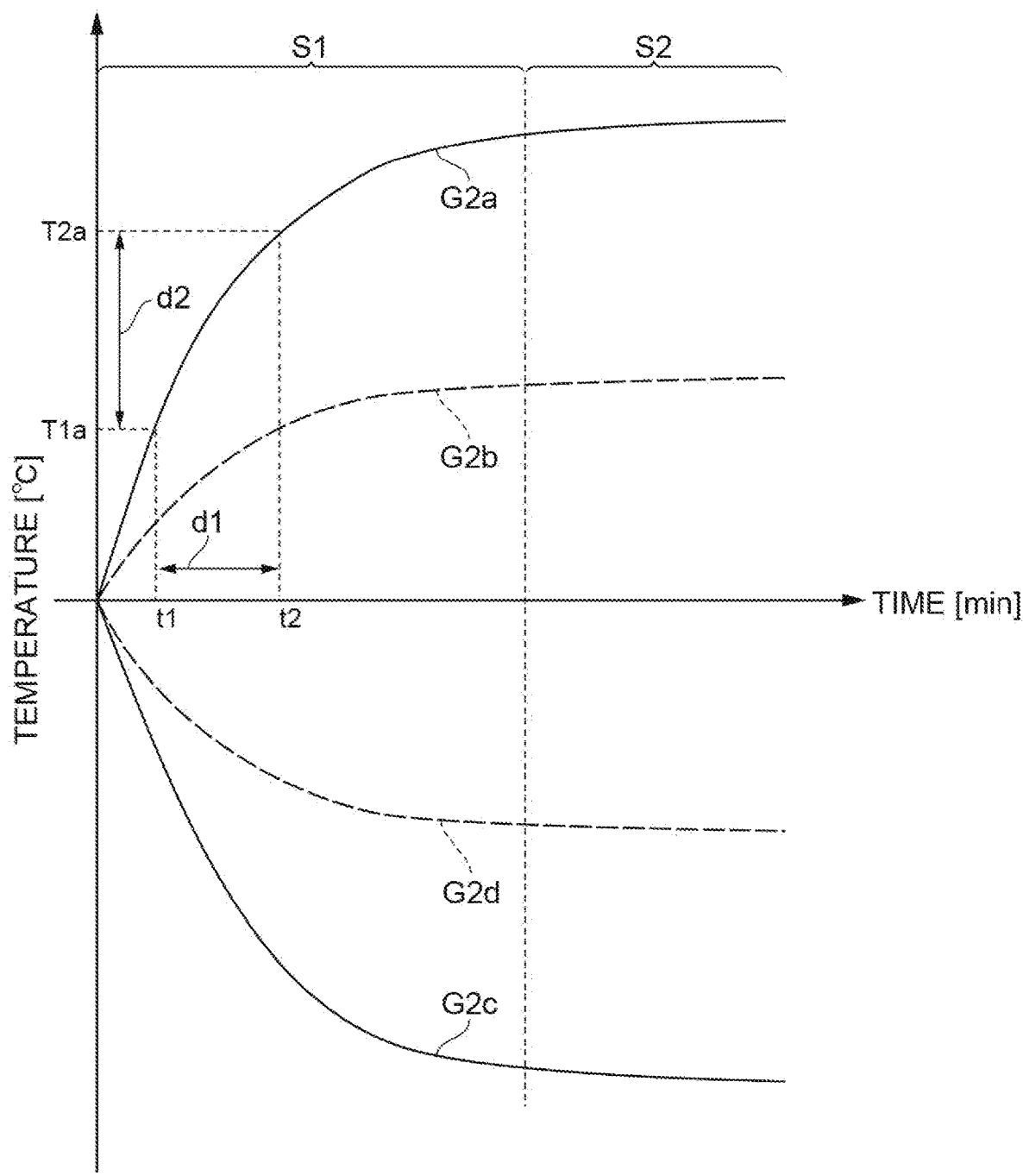
FIG. 2 is a diagram for explaining a principle of obtaining a moisture content.

FIG. 2 shows a temperature history obtained when the thermoelectric element 11 is operated to provide heat from the first heat input/output surface 11a to the soil 100 and dissipate heat of the soil 100 by the second heat input/output surface 11b. A graph G2a and a graph G2b are temperature histories obtained from the first temperature measurement unit 12. A graph G2c and a graph G2d are temperature histories obtained from the second temperature measurement unit 13. A moisture state of the soil 100 denoted by the graph G2a is different from a moisture state of the soil 100 denoted by the graph G2b. Specifically, a moisture content of the soil 100 denoted by the graph G2a is less than a moisture content of the soil 100 denoted by the graph G2b. As can be understood by comparing the graph G2a and the graph G2b, temperatures of them during a steady state period S2 are different when the moisture states are different. A temperature difference that appears during the steady state period S2 is caused by a difference in thermal conductivity of the soil 100. The difference in thermal conductivity of the soil 100 is caused by a difference in moisture content. Therefore, the moisture content can be obtained using the temperature difference that appears during the steady state period S2.

The inventors have found that a difference in thermal properties of the soil 100 caused by a difference in moisture content causes a difference in thermal conductivity and a difference in specific heat. Specifically, if a porosity of the soil 100 is constant, specific heat increases as a proportion of moisture increases. As a result, the thermal conductivity also increases. In thermal properties, a difference in specific heat appears in a temperature change amount per unit time. In the following description, an "temperature change amount" is defined as a temperature change amount per unit time. When the thermoelectric element 11 starts to provide heat, the temperature of the soil 100 in contact with the first heat input/output surface 11a rises. The temperature change amount per unit time appearing in the graph G2a is clearly different from the temperature change amount per unit time appearing in the graph G2b. The inventors have conceived that a moisture content can be obtained by using the temperature change amount per unit time.

Figure 5:
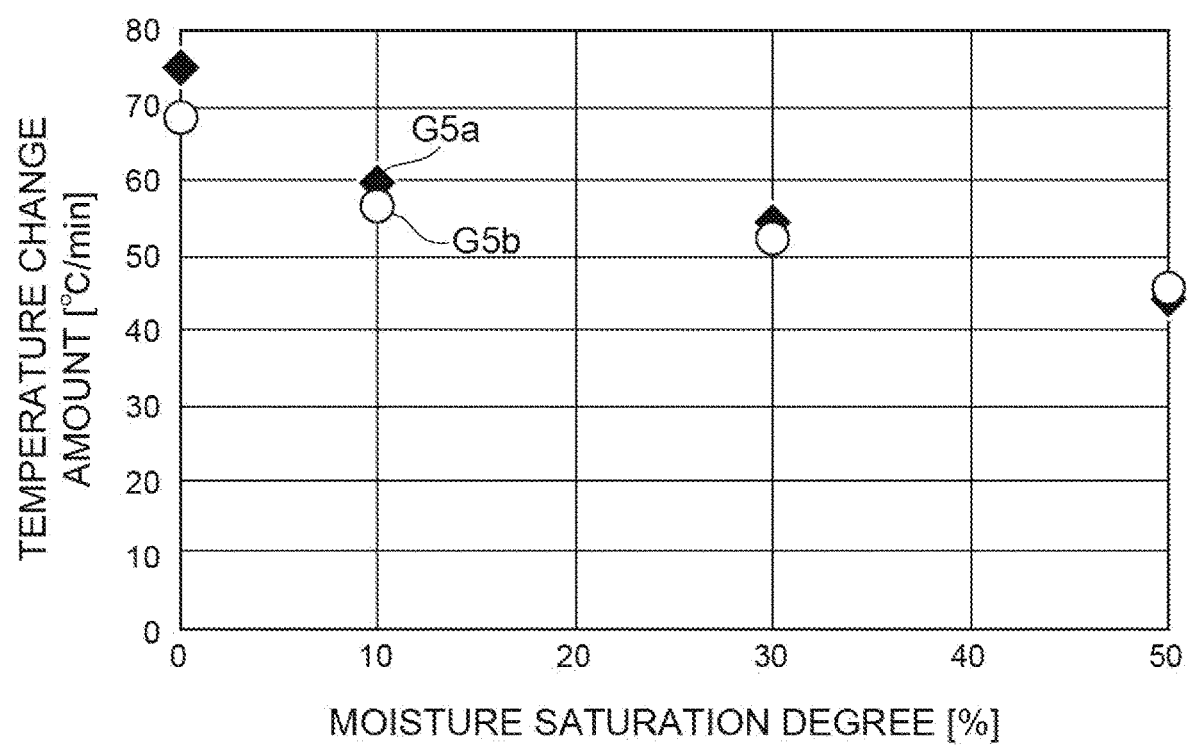
FIG. 5 is a graph showing an example of a relationship between a moisture saturation degree and a temperature change amount.

FIG. 5 is an experiment result in which a temperature change amount was measured using a soil at a predetermined moisture saturation degree as a measurement object. The horizontal axis of the graph represents a moisture saturation degree. Soils with moisture saturation degrees of 0%, 10%, 30%, and 50% were used for the experiment. The vertical axis of the graph represents a temperature change amount. A plot G5a shown in FIG. 5 indicates a temperature history of a cooling side. A plot G5b indicates a temperature history on a heating side. As indicated by the plots G5a and G5b, it was found that a predetermined relationship could be read between the moisture saturation degree and the temperature change amount. Specifically, the temperature change amount decreased as the moisture saturation degree increased. It was also found that there was no significant difference in the relationship between the moisture saturation degree and the temperature change amount in both cooling and heating. The temperature change amount per unit time when the temperature of the soil 100 rises is the same as the temperature change amount per unit time when the temperature of the soil 100 decreases. Therefore, the moisture content can also be obtained using the temperature change amount when the temperature rises. The moisture content can also be obtained using the temperature change amount when the temperature decreases.

When the moisture content is calculated, the temperature change amount per unit time that appears during a transient period S1 has some advantages compared to the temperature change amount per unit time that appears during the steady state period S2. As described above, the difference in the temperature change amount per unit time is based on the difference in specific heat. Specific heat is less susceptible to factors such as an ion concentration of the soil 100. Since specific heat is less susceptible to noise, it is advantageous from the viewpoint of improving measurement accuracy.

When an operation of the thermoelectric element 11 is started, the transient period S1 arises. After the transient period S1, the steady state period S2 arises. The temperature change amount per unit time is obtained during the transient period S1. The temperature of the steady state period S2 is obtained during the steady state period S2. The temperature change amount per unit time obtained in the transient period S1 can be obtained at an earlier timing than that of the temperature in the steady state period S2. It is difficult to clearly determine whether or not the steady state period S2 has been reached. Compared to determining whether or not the steady state period S2 has been reached, it is easier to determine whether it is the transient period S1.

The soil 100 that grows crops is managed under conditions suitable for growing the crops. The conditions suitable for growing crops include a moisture content, an ion concentration, and a temperature. It is desirable to cause the temperature of the soil 100 to fall within a predetermined range. Under such conditions, it is assumed that a temperature immediately after the start of the operation of the thermoelectric element 11 is a desired temperature. Then, the temperature in the transient period S1 deviates less from the desired temperature than the temperature in the steady state period S2. Therefore, an influence of measuring the moisture content on crops can be suppressed.

Figure 3:
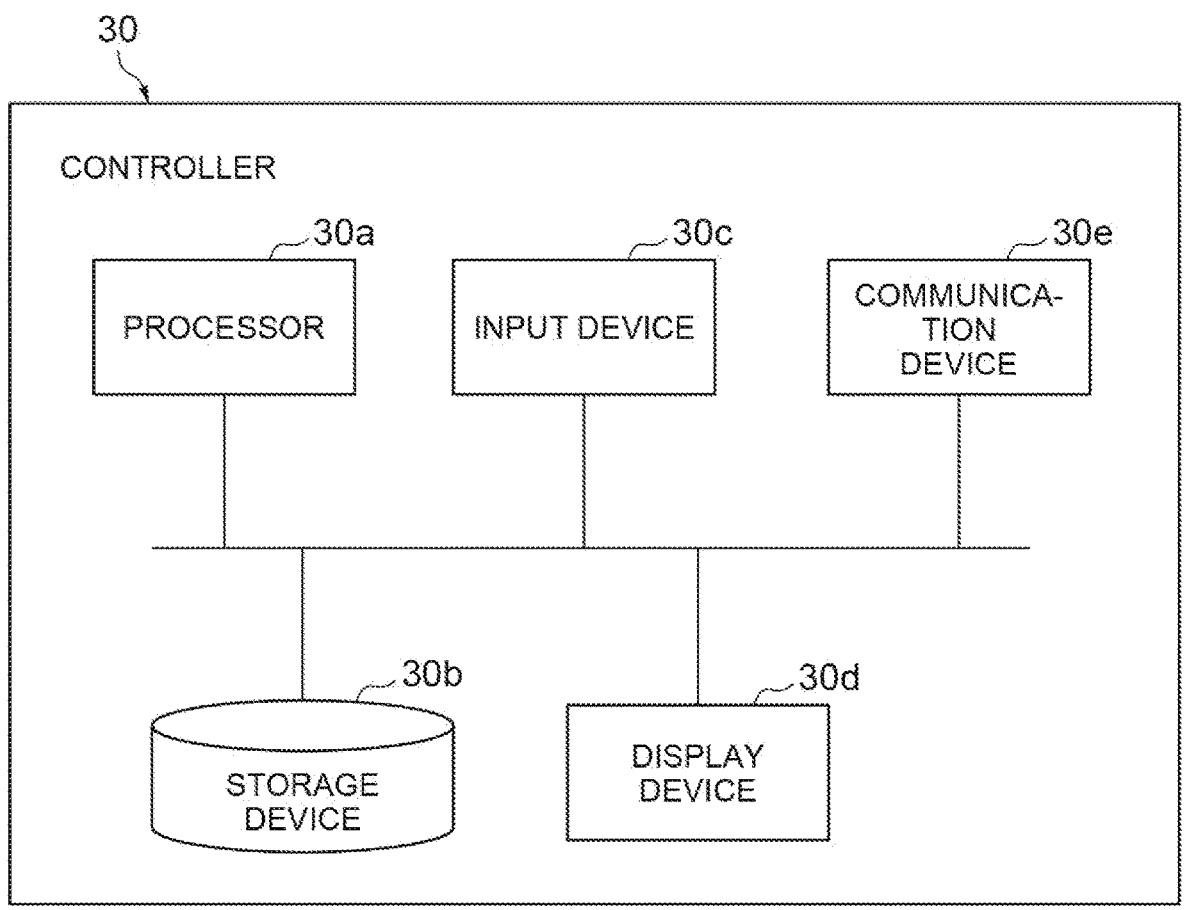
FIG. 3 is a diagram showing an example of a physical configuration of an arithmetic device.

FIG. 3 is a block diagram showing a hardware configuration of the arithmetic device 30. The arithmetic device 30 is a computer. The arithmetic device 30, which is a computer, physically includes one or more processors 30a, a storage device 30b such as a RAM (Random Access Memory) and a ROM (Read Only Memory), an input device 30c such as a keyboard, a display device 30d such as a display, and a communication device 30e serving as a communication interface for transmitting and receiving data. The arithmetic device 30 operates each hardware under the control of processor 30a by causing hardware such as the processor 30a to read a predetermined computer program. The arithmetic device 30 reads data from the storage device 30b. The arithmetic device 30 writes data to the storage device 30b. By these operations, each function of the arithmetic device 30 shown in FIG. 1 is realized. The arithmetic device 30 need not include all of these components.

FIG. 1 is referred to again. The arithmetic device 30 includes a voltage control unit 31, a first data logger 32, a second data logger 33, a storage unit 34, a gradient information acquisition unit 35, an equilibrium temperature acquisition unit 36, and a conversion unit 37.

The voltage control unit 31 outputs a control signal to the power supply device 50. The control signal contains information such as a level of the voltage and a positive or negative polarity of the voltage.

Figure 4:
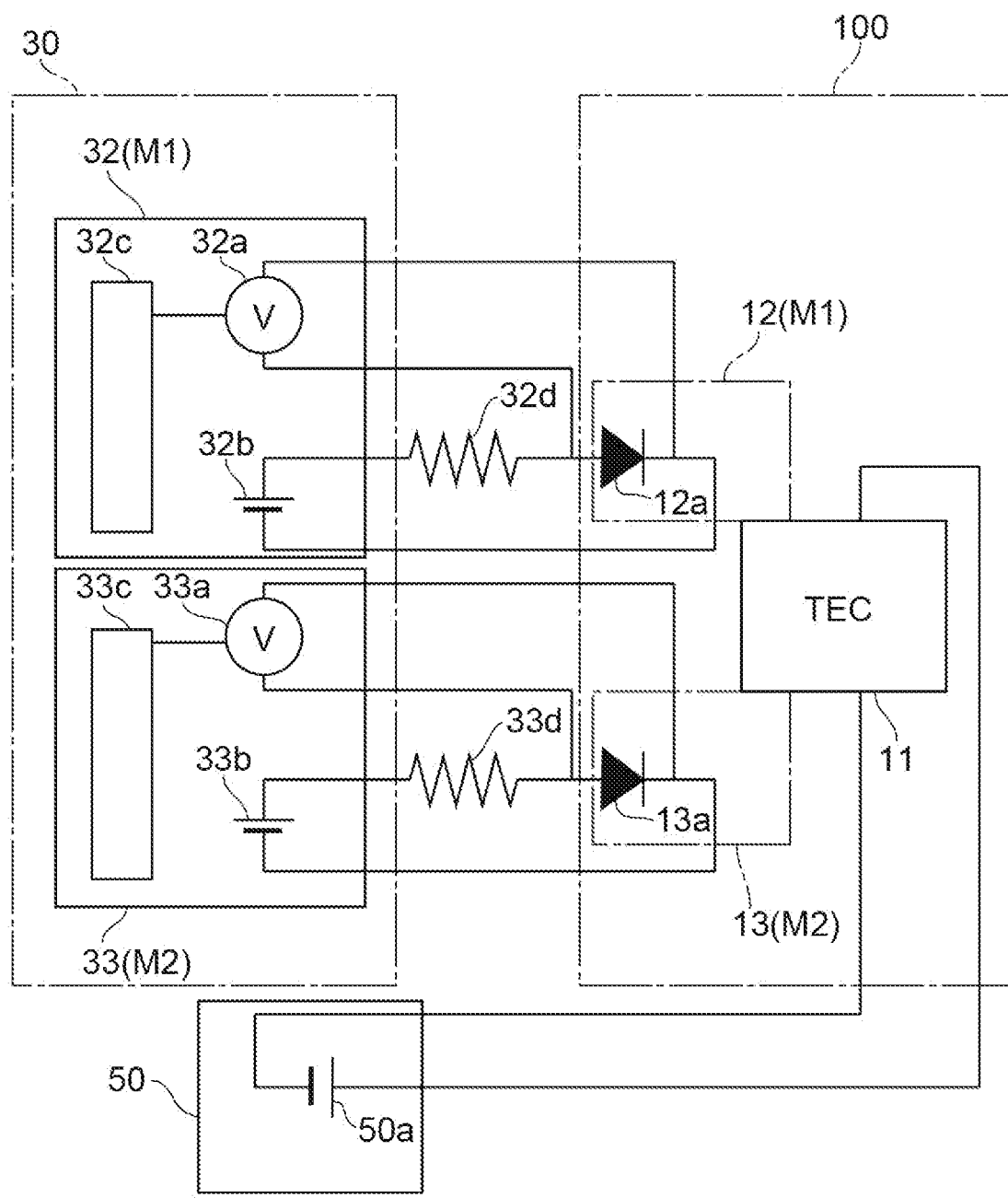
FIG. 4 is a diagram showing an example of an electrical configuration of a temperature acquisition unit included in the moisture sensor of FIG. 1.

As shown in FIG. 4, the first data logger 32 measures a voltage generated in the first temperature measurement unit 12. The first data logger 32 converts the voltage into temperature information. The first data logger 32 outputs the temperature information to the storage unit 34. The first data logger 32 includes a first voltmeter 32a, a first DC power supply 32b, and a first temperature converter 32c. The first voltmeter 32a measures a potential difference (voltage) generated in the first temperature measurement unit 12. The first voltmeter 32a outputs the voltage to the first temperature converter 32c. The first temperature converter 32c converts the voltage input from the first voltmeter 32a into a temperature. A relationship between the voltage and the temperature may be information acquired in advance. The relationship between the voltage and the temperature may have been stored in the storage unit 34. The information indicating the relationship between the voltage and the temperature may be a mathematical expression. The information indicating the relationship between the voltage and the temperature may be a conversion table.

A configuration of the second data logger 33 is the same as that of the first data logger 32. The second data logger 33 also includes a second voltmeter 33a, a second DC power supply 33b, and a second temperature converter 33c. Operations of the second voltmeter 33a and the like are the same as those of the first voltmeter 32a and the like. Therefore, detailed description of the second voltmeter 33a, the second DC power supply 33b, and the second temperature converter 33c will be omitted.

The first temperature measurement unit 12 and the first data logger 32 constitute a first temperature information acquisition unit M1. The second temperature measurement unit 13 and the second data logger 33 constitute a second temperature information acquisition unit M2.

The first temperature measurement unit 12 includes a first diode 12a. When a constant voltage is input to a diode, a predetermined potential difference (voltage) is generated between an input and an output of the diode. The voltage generated between the input and output of the diode changes according to a temperature. For example, such a relationship that the temperature decreases as the voltage increases can be obtained by conducting a prior test. Therefore, a temperature can be obtained using the voltage. It is possible to know the temperature of the diode by measuring the voltage thereof.

An input of the first diode 12a is connected to a positive electrode of the first DC power supply 32b via a first resistor 32d. The first resistor 32d is disposed between the first diode 12a and the first DC power supply 32b. An output of the first diode 12a is connected to a negative electrode of the first DC power supply 32b. The first voltmeter 32a is connected to the input of the first diode 12a and the output of the first diode 12a. The first voltmeter 32a outputs information on the voltage to the first temperature converter 32c. The conversion unit 37 converts the voltage into a temperature. The conversion unit 37 outputs temperature information.

Similarly to the first temperature measurement unit 12, the second temperature measurement unit 13 also includes a second diode 13a. A connection configuration and an operation of the second diode 13a are the same as those of the first temperature information acquisition unit M1. Therefore, detailed description of the second temperature measurement unit 13 will be omitted.

The storage unit 34 corresponds to the storage device 30b shown in FIG. 3. The storage unit 34 receives first temperature information D1 from the first data logger 32. The storage unit 34 receives second temperature information D2 from the second data logger 33. The storage unit 34 is referred to by the gradient information acquisition unit 35. The storage unit 34 outputs the first temperature information D1 and the second temperature information D2 to the gradient information acquisition unit 35. The storage unit 34 is referred to by the conversion unit 37. The storage unit 34 outputs conversion information D3 to the storage unit 34.

The storage unit 34 stores at least the first temperature information D1, the second temperature information D2, and the conversion information D3. The first temperature information D1 indicates a temporal change of a first temperature (for example, the graph G2a in FIG. 2). The first temperature information D1 is based on an output of the first temperature information acquisition unit M1. The second temperature information D2 indicates a temporal change of a second temperature (for example, the graph G2c in FIG. 2). The second temperature information D2 is based on an output of the second temperature information acquisition unit M2. The conversion information D3 is information for converting a gradient of the temperature change amount into the moisture content. The conversion information D3 may be a mathematical expression in which the gradient of the temperature change amount is used as an input variable and the moisture content is used as a dependent variable. The conversion information D3 may be a conversion table in which the moisture content corresponding to the gradient of the temperature change amount is summarized.

The gradient information acquisition unit 35 acquires first gradient information using the first temperature information D1. There is no particular limitation on a specific content of processing for acquiring the first gradient information. For example, as shown in FIG. 2, the transient period S1 and the steady state period S2 are distinguished in the first temperature information D1 (graph G2a). Next, in the transient period S1, a predetermined time width d1 (t2−t1) and a temperature difference d2 (T2a−T1a) occurring in the time width d1 are acquired. The time width d1 may be appropriately set on the basis of arbitrary conditions. For example, a starting point for acquiring the gradient may be set in consideration of the time difference based on the thermal properties of the thermoelectric element 11 with a time point at which application of the current is started as a reference. The "starting point for acquiring the gradient" is, for example, a temperature T1a in FIG. 2. A timing at which a change in temperature is detected may be set as the starting point for acquiring the gradient. It is not limited to the processing of obtaining the temperature difference d2 on the basis of the time width d1. The time width d1 may be obtained on the basis of the temperature difference d2. The first gradient information is obtained using the time width d1 and the temperature difference d2. Also for the second temperature information D2, the gradient information acquisition unit 35 performs the same processing. As a result, the gradient information acquisition unit 35 acquires the first gradient information and the second gradient information. The gradient information acquisition unit 35 may output the first gradient information and the second gradient information to the storage unit 34. The gradient information acquisition unit 35 may output the first gradient information and the second gradient information to the conversion unit 37.

Information output by the gradient information acquisition unit 35 is not limited to the first gradient information and the second gradient information. For example, the gradient information acquisition unit 35 may output a difference between the first gradient information and the second gradient information as total gradient information.

The equilibrium temperature acquisition unit 36 acquires first equilibrium temperature information using the first temperature information D1. There is no particular limitation on a specific content of processing for acquiring the first equilibrium temperature information. The equilibrium temperature acquisition unit 36 acquires second equilibrium temperature information as a result of performing the same processing for the second temperature information D2. The equilibrium temperature acquisition unit 36 may be provided as necessary. It is also possible for the arithmetic device 30 to omit the equilibrium temperature acquisition unit 36.

The conversion unit 37 converts the first gradient information into first moisture information. The conversion unit 37 converts the second gradient information into second moisture information. The conversion unit 37 receives the first gradient information from the gradient information acquisition unit 35 or the storage unit 34. The conversion unit 37 receives the conversion information D3 from the storage unit 34. The conversion unit 37 converts the first gradient information into the first moisture information by using the conversion information D3. Also for the second gradient information, the conversion unit 37 performs the same processing. The conversion unit 37 obtains total moisture information using the first moisture information and the second moisture information. There is no particular limitation on the processing of obtaining the total moisture information from the first moisture information and the second moisture information. For example, an average value of the first moisture information and the second moisture information may be used as the total moisture information.

Hereinafter, an operation and effects of the soil moisture sensor 1 will be described while describing a background on the soil moisture sensor 1 of the first embodiment, problems in conventional technologies, and the like as an example.

In the fields of agriculture and disaster prevention, it is important to measure a moisture content contained in the soil 100 (moisture content in the soil). As a technology for measuring a moisture content in a soil, there is a sensor employing a TDR method that utilizes reflection of electromagnetic waves. As another technology for measuring a moisture content in a soil, there is also a sensor that employs a capacitance method that detects a difference in relative dielectric constant by measuring electrical impedance. All of these sensors measure a relative dielectric constant obtained from a combined capacitance of a substance. However, the relative dielectric constant is affected by a concentration of ions in water. In measuring the moisture content, differences in ion concentration result in noise.

In view of the circumstances described above, the soil moisture sensor 1 includes the thermoelectric element 11 disposed in the soil 100 and capable of changing a temperature of the soil 100, the first temperature information acquisition unit M1 acquiring the first temperature information D1 that indicates a temporal change in temperature of the soil 100 due to an operation of the thermoelectric element 11, a second temperature information acquisition unit M2 acquiring the second temperature information D2 that indicates a temporal change in temperature of the soil 100 due to an operation of the thermoelectric element 11, and an arithmetic device 30 obtaining moisture information on the basis of the temperature information. The arithmetic device 30 includes the gradient information acquisition unit 35 that acquires a temperature change amount per unit time using the first temperature information D1 and the second temperature information D2, and the conversion unit 37 that converts the temperature change amount into a moisture content using the conversion information D3 indicating a relationship between the temperature change amount and the moisture content.

The soil moisture sensor 1 obtains a temperature change amount as information when it performs an operation of changing the temperature of the soil 100. The temperature change amount is related to information on moisture contained in the soil 100. The temperature change amount is based on specific heat of the soil 100. The specific heat of the soil 100 is a physical quantity. Therefore, the temperature change amount is less susceptible to a factor of a disturbance. Therefore, stable measurement results can be obtained by obtaining information on the moisture using the temperature change amount caused by specific heat.

The soil moisture sensor 1 can obtain necessary measurement information in a short period of time. As a result, the measurement can be performed using only specific heat and thermal conductivity without generating Joule heat. According to this configuration, the moisture information can be measured without increasing an average temperature of the heating part and the cooling part.

A sensor employing the TDR method that utilizes reflection of electromagnetic waves requires a signal with a high sampling frequency during measurement. In order to generate the signal, the sensor employing the TDR method has a complicated and large system. On the other hand, the soil moisture sensor 1 of the first embodiment does not require a signal with a high sampling frequency as required in a device with the TDR method. As a result, the system can be simplified. Further, the soil moisture sensor 1 can also be miniaturized. Therefore, the soil moisture sensor 1 can be suitably applied to precision agriculture in which compact sensors capable of wide-range and multi-point measurement are required.

The embodiment of the present invention has been described above. The soil moisture sensor 1 of the present invention is not limited to the above-described embodiment.

The soil moisture sensor 1 of the first embodiment is not limited to use in precision agriculture with a high nutrient concentration. For example, it can be used for a soil with a high concentration of contamination and for calibrating a moisture content measurement sensor based on impedance. Further, a measurement object is not limited to the soil 100. For example, application to the field of skin regenerative medicine is also possible. As an example, it can be applied to a measurement of a moisture content under the high ion concentration such as physiological saline.

The soil moisture sensor 1 that uses thermal properties of the measurement object may be applied to a multimodal sensor that measures a plurality of soil characteristic values such as a temperature, an ion concentration, and a pH value of the soil 100 in real time.

The soil moisture sensor 1 may obtain the moisture content using only the temperature change amount per unit time or may obtain the moisture content by combining the temperature change amount per unit time and the temperature in a steady state.

In the soil moisture sensor 1 of the first embodiment, a configuration in which the first temperature measurement unit 12 is directly attached to the first heat input/output surface 11a has been exemplified. The first temperature measurement unit 12 does not necessarily have to be in direct contact with the first heat input/output surface 11a. For example, the first temperature measurement unit 12 may be attached to the first heat input/output surface 11a via a member such as a heat transfer grease or an adhesive. Any member may be disposed between the first temperature measurement unit 12 and the first heat input/output surface 11a. The soil 100, which is a measurement object, may be present between the first temperature measurement unit 12 and the first heat input/output surface 11a. When the sensor unit 10 is taken out from the soil 100, a gap may be present between the first temperature measurement unit 12 and the first heat input/output surface 11a. If the gap between the first temperature measurement unit 12 and the first heat input/output surface 11a is several centimeters (for example, 4 centimeters) or less, the same effects as the above-described soil moisture sensor 1 of the first embodiment can be obtained. The same applies to the relationship between the second temperature measurement unit 13 and the second heat input/output surface 11b.

Second Embodiment

A soil moisture sensor according to a second embodiment will be described. The soil moisture sensor 1 described above utilized the fact that the moisture content contained in the soil 100 corresponded to the specific heat to measure the moisture content. Differences in specific heat corresponding to the moisture contents can be evaluated using various methods. The soil moisture sensor 1 of the first embodiment described above was evaluated using a degree of temperature rise (temperature change amount per unit time) when heat was applied to the soil 100. Then, the soil moisture sensor 1 of the first embodiment converted the temperature change amount per unit time into the moisture content.

Similarly to the soil moisture sensor 1 of the first embodiment, a soil moisture sensor 1A of the second embodiment also utilizes the fact that a moisture content contained in a soil 100 corresponds to specific heat to measure the moisture content. On the other hand, the soil moisture sensor 1A uses a method different from that of the soil moisture sensor 1 of the first embodiment to evaluate a difference in specific heat corresponding to the moisture content. Hereinafter, the soil moisture sensor 1A will be described.

Figure 6:
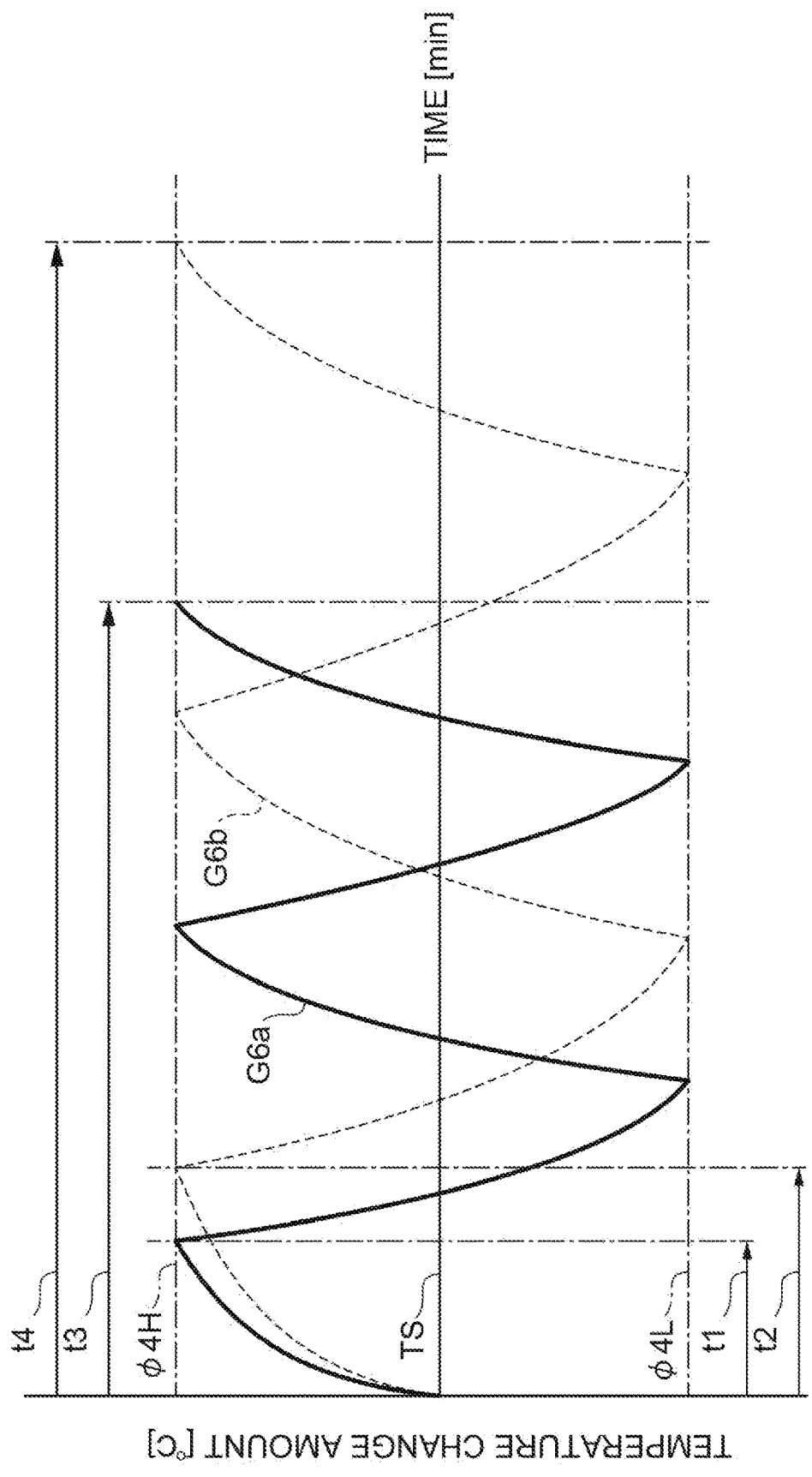
FIG. 6 is a diagram for explaining a principle of measurement employed by a moisture sensor of a second embodiment.

First, a principle of measuring a moisture content employed by the soil moisture sensor 1A will be described. The graph of FIG. 6 shows a temporal change of a temperature change amount of the soil 100. The horizontal axis of FIG. 6 represents an elapsed time with the start of heating due to a thermoelectric element 11 as a reference. The vertical axis in FIG. 6 represents a temperature change amount in the soil 100. The graph G6a shows a temporal change of a temperature change amount in the soil 100 with a low moisture content. The graph G6b shows a temporal change of a temperature change amount in the soil 100 with a high moisture content.

For example, it is necessary to focus on the graph G6a. As shown in the graph G6a, the soil moisture sensor 1A repeats heating and cooling of the soil 100 a plurality of times. The soil moisture sensor 1A switches an operation of the thermoelectric element 11 from heating to cooling on condition that the temperature change amount of the soil 100 reaches a predetermined upper threshold value $\phi 4H$. Also, the soil moisture sensor 1A switches the operation of the thermoelectric element 11 from cooling to heating on condition that the temperature change amount of the soil 100 reaches a predetermined lower threshold value $\phi 4L$.

A moisture content contained in the soil 100 affects specific heat of the soil 100. Specifically, when the moisture content is low, the specific heat is low. Therefore, the soil 100 with a low moisture content has a large temperature change amount. For example, in a case of heating, a time t1 until reaching the upper threshold value $\phi 4H$ is also short. On the other hand, when the moisture content is high, the specific heat is high. Therefore, the soil 100 with a high moisture content has a small temperature change amount. In a case of heating, a time t2 until reaching the upper threshold value $\phi 4H$ is longer than the time t1.

The difference in time until reaching the threshold value, that occurs according to the difference in moisture content, is integrated each time the operations of heating and cooling are repeated. As a result, times t3 and t4 until the given number of times of the predetermined switching operations is reached differ according to the moisture content contained in the soil 100. For example, the time t4 until the given number of times is reached in a case in which the moisture content of the soil 100 is high (graph G6b) is longer than the time t3 until the given number of times is reached in a case in which the moisture content of the soil 100 is low (graph G6a). Therefore, the soil moisture sensor 1A evaluates a difference in specific heat corresponding to the moisture content using the times t3 and t4 until the given number of times of the switching operations is reached.

Figure 7:
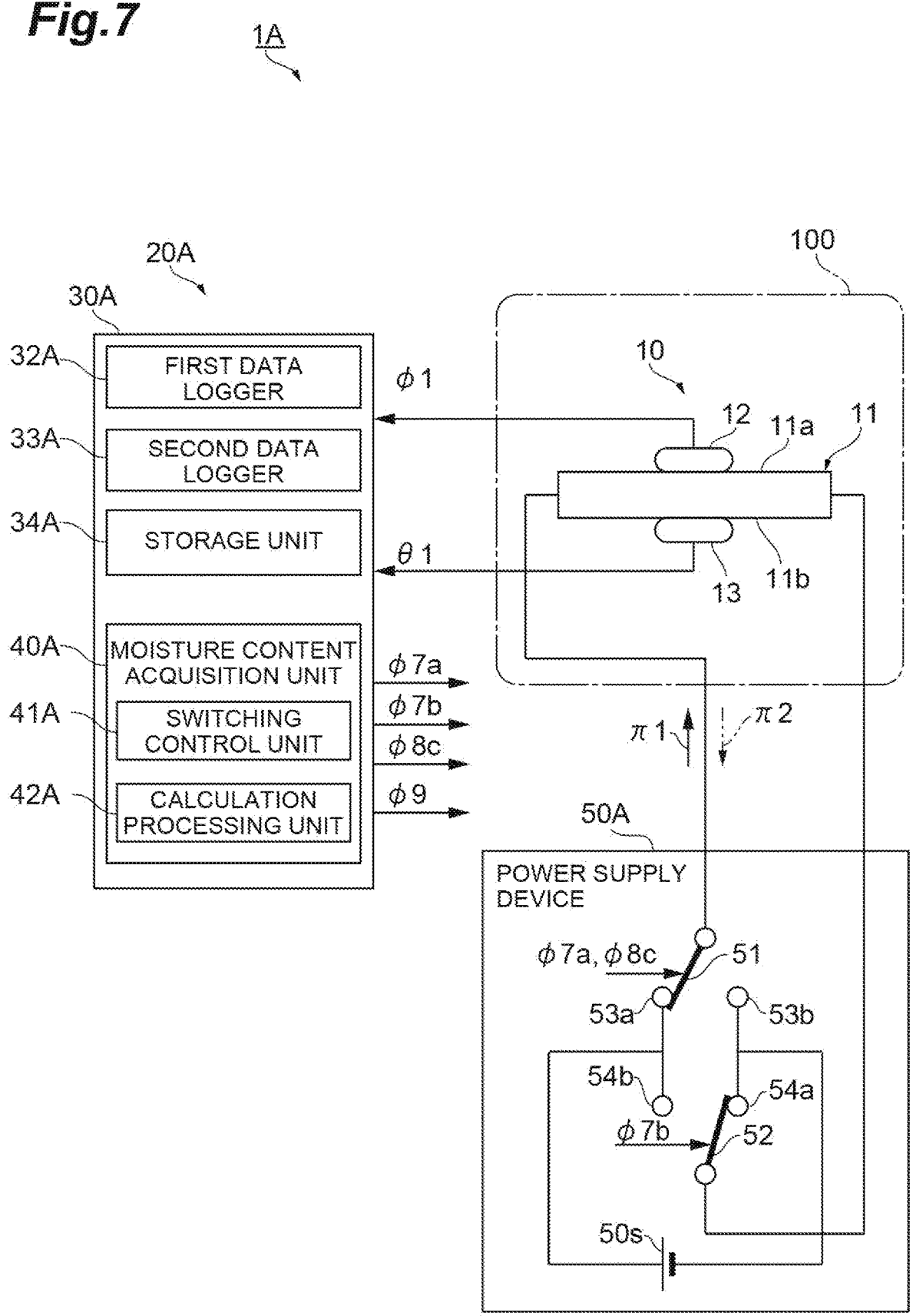
FIG. 7 is a diagram schematically showing a configuration of the moisture sensor of the second embodiment.

As shown in FIG. 7, the soil moisture sensor 1A includes a sensor unit 10 and a control unit 20A. The sensor unit 10 is the same as the sensor unit 10 of the soil moisture sensor 1 in the first embodiment. Therefore, detailed description of the sensor unit 10 will be omitted. The control unit 20A includes an arithmetic device 30A and a power supply device 50A. The arithmetic device 30A receives a first voltage $\phi 1$ output by a first temperature measurement unit 12. The arithmetic device 30A receives a second voltage $\theta 1$ output by a second temperature measurement unit 13. The arithmetic device 30A outputs a moisture content $\phi 9$ by using the first voltage $\phi 1$ and the second voltage $\theta 1$.

The power supply device 50A provides either one of a first current $\pi 11$ and a second current $\pi 2$ to the thermoelectric element 11. A direction of the first current $\pi 1$ is opposite to a direction of the second current $\pi 2$. The power supply device 50A switches a direction of the current by switching a polarity of the voltage connected to the thermoelectric element 11. For example, the power supply device 50A includes a switch 51, a switch 52, and a DC power supply 50s. The power supply device 50A switches a polarity of the DC power supply 53 connected to the thermoelectric element 11 by controlling the switch 51 and the switch 52. Terminals 53a and 53b connected to the switch 51 are switched according to control signals $\phi 7a$ and $\phi 8c$. The switch 51 maintains connection to the terminal 53a or terminal 53b until it receives the next control signals $\phi 7a$ and $\phi 8c$. Terminals 54a and 54b connected to the switch 52 are switched according to a control signal $\phi 7b$. The switch 52 maintains connection to the terminal 54a or terminal 54b until it receives the next control signal $\phi 7b$. The control signals $\phi 7a$, $\phi 7b$, and $48c$ are provided from the arithmetic device 30A. Further, a circuit configuration of the power supply device 50A shown in FIG. 7 is an example. Any circuit configuration may be employed as the circuit configuration of the power supply device 50A as long as it can switch a direction of the current supplied to the thermoelectric element 11.

Figure 8:
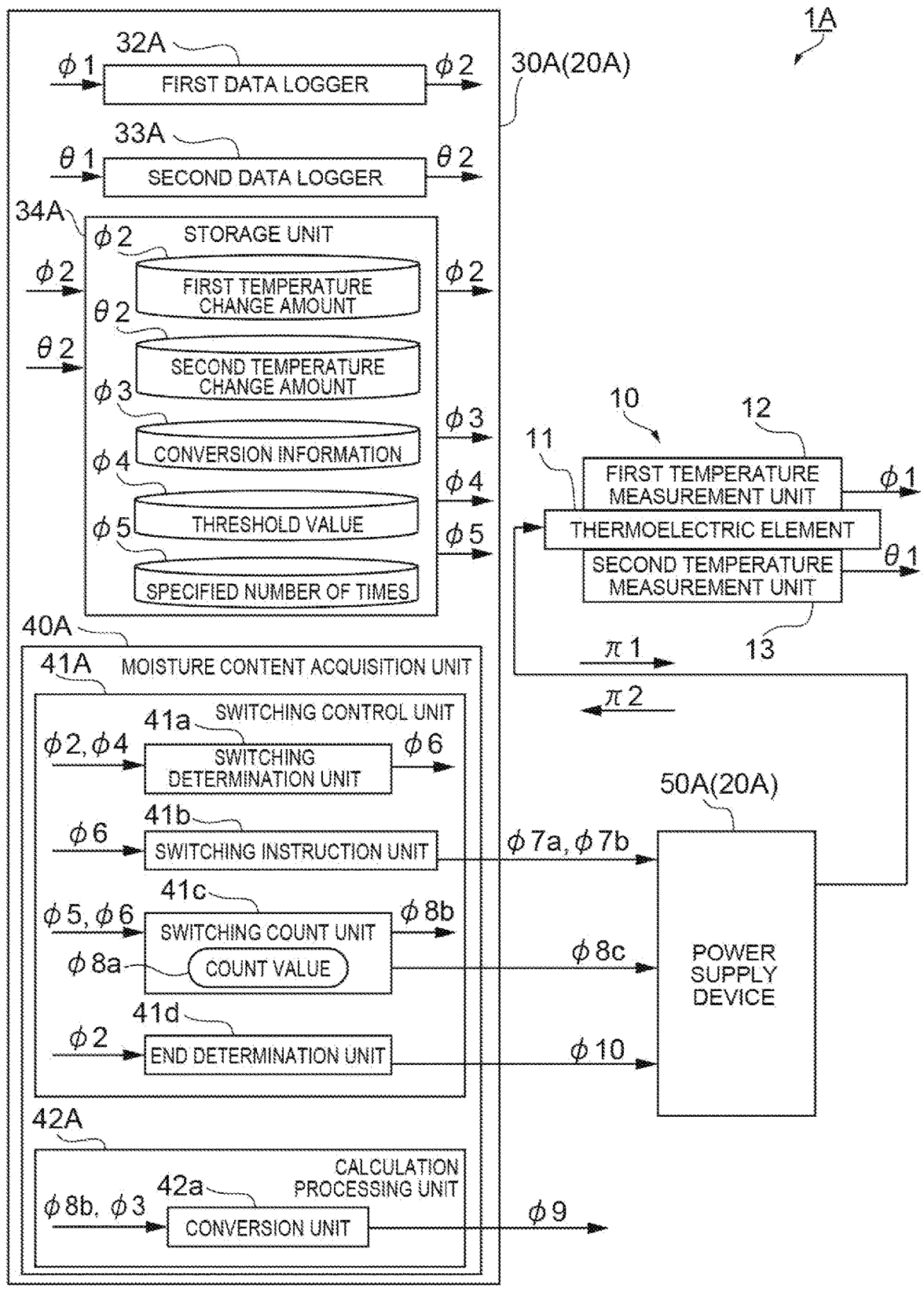
FIG. 8 is a diagram showing a configuration of the moisture sensor shown in FIG. 7 in detail.

As shown in FIG. 8, the arithmetic device 30A includes a first data logger 32A, a second data logger 33A, a storage unit 34A, and a moisture content acquisition unit 40A.

The first data logger 32A receives the first voltage $\phi 1$. The first data logger 32A converts the first voltage $\phi 1$ into a first temperature change amount $\phi 2$. The first data logger 32A outputs the first temperature change amount $\phi 2$. The second data logger 33A receives the second voltage $\theta 1$. The second data logger 33A converts the second voltage $\theta 1$ into a second temperature change amount $\theta 2$. The second data logger 33A outputs the second temperature change amount $\theta 2$.

Further, in the following description, the "first temperature change amount $\phi 2$" and the "second temperature change amount $\theta 2$" are each defined as a difference from a reference temperature TS when a temperature of the soil 100 immediately before the start of measurement is the reference temperature TS.

The storage unit 34A receives the first temperature change amount $\phi 2$. The storage unit 34A stores the first temperature change amount $\phi 2$ in association with time. The storage unit 34A receives the second temperature change amount $\theta 2$. The storage unit 34A stores the second temperature change amount $\theta 2$ in association with time.

The storage unit 34A has some values for processing of calculating the moisture content $\phi 9$. The storage unit 34A stores conversion information $\phi 3$ for converting an evaluation value into the moisture content $\phi 9$ as the value for the processing of calculating the moisture content $\phi 9$.

The storage unit 34A has some values for controlling the sensor unit 10. For example, the storage unit 34A stores a plurality of threshold values $\phi 4$ as the value for controlling the sensor unit 10. The storage unit 34A holds a specified number of times $\phi 5$ as the value for controlling the sensor unit 10. The "specified number of times $\phi 5$" is the number of switching performed in one measurement operation of the moisture content. The specified number of times $\phi 5$ may be defined as one switching from heating to cooling. Similarly, the specified number of times $\phi 5$ may be defined as one switching from cooling to heating. Also, one switching from heating to cooling and one switching from cooling to heating may be collectively defined as one switching of the specified number of times $\phi 5$.

The moisture content acquisition unit 40A receives the first temperature change amount $\phi 2$ from the storage unit 34A. The moisture content acquisition unit 40A generates the control signals $\phi 7a$, $\phi 7b$, and $\phi 8c$ for the power supply device 50A by using the first temperature change amount $\phi 2$. The moisture content acquisition unit 40A generates the moisture content $\phi 9$ by using the first temperature change amount $\phi 2$.

The moisture content acquisition unit 40A includes a switching control unit 41A and a calculation processing unit 42A. The switching control unit 41A receives the first temperature change amount $\phi 2$ and the threshold values $\phi 4$ from the storage unit 34A. The switching control unit 41A generates the control signals $\phi 7a$, $\phi 7b$, and $\phi 8c$ for the power supply device 50A using the first temperature change amount $\phi 2$ and the threshold values $\phi 4$. The calculation processing unit 42A receives an elapsed time $\phi 8b$ from the switching control unit 41A. Further, the calculation processing unit 42A receives the conversion information $\phi 3$ from the storage unit 34A. The calculation processing unit 42A converts the elapsed time $\phi 8b$ to the moisture content $\phi 9$ using the conversion information $\phi 3$.

The switching control unit 41A includes a switching determination unit 41a, a switching instruction unit 41b, and a switching count unit 41c.

The switching determination unit 41a receives the first temperature change amount $\phi 2$ from the storage unit 34A. Further, the switching determination unit 41a receives the threshold value $\phi 4$ from the storage unit 34A. The switching determination unit 41a determines whether or not the first temperature change amount $\phi 2$ has reached the threshold value $\phi 4$. The switching determination unit 41a outputs a determination result $\phi 6$ according to the determination result. The determination result $\phi 6$ is either information indicating that the first temperature change amount $\phi 2$ has reached the threshold value $\phi 4$ or information indicating that the first temperature change amount $\phi 2$ has not reached the threshold value $\phi 4$.

Here, the threshold values ϕ4 will be described in detail. The threshold values ϕ4 are conditions for alternately switching between heating and cooling of the thermoelectric element 11. There are some setting methods for the threshold values ϕ4. In the present embodiment, three setting methods are exemplified.

<First Setting Method>

Figure 9:
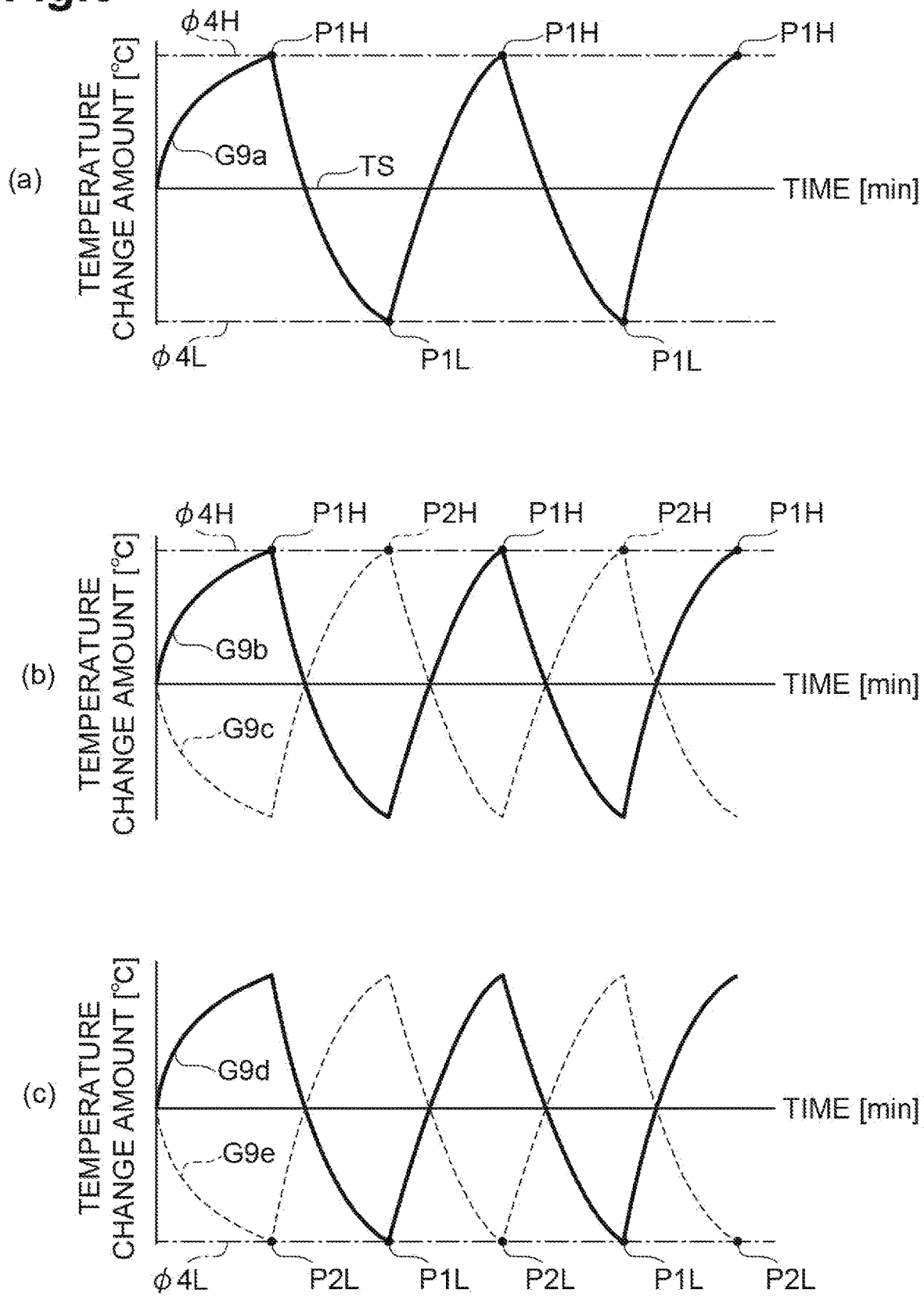
FIG. 9(a) is a diagram showing a first setting method for a threshold value.
FIG. 9(b) is a diagram showing a second setting method for a threshold value.
FIG. 9(c) is a diagram showing a third setting method for a threshold value.

A first setting method is utilized for control of only switching the first temperature change amount ϕ2. In the first setting method, the second temperature change amount θ2 is not utilized for control of the switching. The graph G9a in FIG. 9(a) shows the first temperature change amount ϕ2. The first setting method employs two threshold values. The first setting method employs the upper threshold value ϕ4H and the lower threshold value ϕ4L.

The upper threshold value ϕ4H is higher than, for example, the reference temperature TS of the soil 100 immediately before the start of measurement. As an example, the upper threshold value ϕ4H is higher than the reference temperature TS of the soil 100 immediately before the start of measurement by 4 degrees. When the soil 100 is heated by the thermoelectric element 11 and the first temperature change amount ϕ2 reaches the upper threshold value ϕ4H (see a reference sign P1H), the operation of the thermoelectric element 11 is switched from heating to cooling.

The lower threshold value ϕ4L is lower than the reference temperature TS of the soil 100 immediately before the start of measurement. As an example, the lower threshold value ϕ4L is lower than the reference temperature TS of the soil 100 immediately before the start of measurement by 4 degrees. When the soil 100 is cooled by the thermoelectric element 11 and the first temperature change amount ϕ2 reaches the lower threshold value ϕ4L (see a reference sign P1L), the operation of the thermoelectric element 11 is switched from cooling to heating.

When the first setting method is employed, the temperature of the soil 100 with which a first heat input/output surface 11a is in contact can be reliably controlled. Specifically, the first temperature change amount ϕ2 of the soil 100 with which the first heat input/output surface 11a is in contact does not exceed the upper threshold value ϕ4H. Similarly, the first temperature change amount ϕ2 of the soil 100 with which the first heat input/output surface 11a is in contact does not exceed the lower threshold value ϕ4L.

<Second Setting Method>

A second setting method is utilized for control of switching the first temperature change amount ϕ2 and the second temperature change amount θ2. The graph G9b in FIG. 9(b) shows the first temperature change amount ϕ2. The graph G9b in FIG. 9(b) shows the second temperature change amount θ2. The second setting method employs one upper threshold value ϕ4H.

When the soil 100 is heated by the first heat input/output surface 11a of the thermoelectric element 11 and the first temperature change amount ϕ2 reaches the upper threshold value ϕ4H, the operation of the thermoelectric element 11 is switched (see a reference sign P1H). Due to the switching of the operation, heating of the soil 100 due to a second heat input/output surface 11b of the thermoelectric element 11 is started. That is, the second temperature change amount θ2 by the second temperature measurement unit 13 provided on the second heat input/output surface 11b starts to rise. Then, when the second temperature change amount θ2 reaches the upper threshold value ϕ4H, the operation of the thermoelectric element 11 is switched (see a reference sign P2H).

When the second setting method is employed, the first temperature change amount ϕ2 of the soil 100 with which the first heat input/output surface 11a is in contact does not exceed the upper threshold value ϕ4H. Similarly, the second temperature change amount θ2 of the soil 100 with which the second heat input/output surface 11b is in contact does not exceed the upper threshold value ϕ4H.

<Third Setting Method>

In the second setting method, the first temperature change amount ϕ2 and the second temperature change amount θ2 have been compared with the upper threshold value ϕ4H. In a third setting method, the first temperature change amount ϕ2 and the second temperature change amount θ2 are compared with the lower threshold value ϕ4L as shown in FIG. 9(c). That is, when the first temperature change amount ϕ2 reaches the lower threshold value ϕ4L (see a reference sign P1L), the operation of the thermoelectric element 11 is switched. Similarly, when the second temperature change amount θ2 reaches the lower threshold value ϕ4L (see a reference sign P2L), the operation of the thermoelectric element 11 is switched.

When the third setting method is employed, the first temperature change amount ϕ2 of the soil 100 with which the first heat input/output surface 11a is in contact does not exceed the lower threshold value ϕ4L. Similarly, the temperature θ2 of the soil 100 with which the second heat input/output surface 11b is in contact does not exceed the lower threshold value ϕ4L.

FIG. 8 is referred to again. The switching instruction unit 41b receives the determination result 46 from the switching determination unit 41a. When the switching instruction unit 41b receives the determination result ϕ6 indicating that the threshold value ϕ4 has been reached, the switching instruction unit 41b outputs the control signals ϕ7a and ϕ7b for switching a direction of the current to the power supply device 50A. When the switching instruction unit 41b receives the determination result ϕ6 indicating that the threshold value ϕ4 has not been reached, the switching instruction unit 41b need not output any signal to maintain the direction of the current.

The switching count unit 41c receives the determination result 46 from the switching determination unit 41a. When the switching count unit 41c receives the determination result 46 indicating that the threshold value ϕ4 has been reached, the switching count unit 41c updates a count value ϕ8a. When the switching instruction unit 41b receives the determination result ϕ6 indicating that the threshold value ϕ4 has not been reached, the switching instruction unit 41b does not update the count value ϕ8a.

Further, the switching count unit 41c determines whether or not the count value ϕ8a of switching has reached the specified number of times ϕ5. When the count value ϕ8a of switching reaches the specified number of times ϕ5, the switching count unit 41c outputs the elapsed time ϕ8b until reaching the specified number of times ϕ5. The elapsed time ϕ8b is an evaluation value from which a difference in specific heat corresponding to the moisture content can be evaluated. Therefore, the elapsed time ϕ8b can be converted into the moisture content ϕ9. Further, when the count value ϕ8a of switching reaches the specified number of times ϕ5, the switching count unit 41c outputs the signal ϕ8c for stopping an output of the power supply device 50A.

The calculation processing unit 42A includes a conversion unit 42a. The conversion unit 42a receives the elapsed time ϕ8b from the switching count unit 41c. Further, the conversion unit 42a receives the conversion information ϕ3 from the storage unit 34. The conversion unit 42a converts the elapsed time ϕ8b to the moisture content ϕ9 using the conversion information ϕ3. The conversion unit 42a outputs the moisture content ϕ9.

<Operation Flow of Soil Moisture Sensor of Second Embodiment>

Next, an operation of the soil moisture sensor 1A will be described. FIG. 10 is a flowchart showing the operation of the soil moisture sensor 1A. The operation shown in FIG. 10 is a case in which the first setting method described above is employed.

First, the threshold values ϕ4 are set (S11). For example, in S11, the upper threshold value ϕ4H and the lower threshold value ϕ4L are set. Next, the first temperature change amount ϕ2 is obtained (S12).

Next, it is determined whether or not the first temperature change amount ϕ2 has reached the upper threshold value ϕ4H (S13). As a result of executing S13, when the first temperature change amount ϕ2 is determined to have reached the upper threshold value ϕ4H (S13: YES), a direction of the current is switched (S14). When the direction of the current is switched, an operation of the first heat input/output surface 11a is switched from heating to cooling. After S14 is executed, the count value of the switching operation is updated (S15). As a result of executing S13, when the first temperature change amount ϕ2 is determined to have not reached the upper threshold value ϕ4H (S13: NO), the direction of the current is not switched. Then, after a predetermined period of time has elapsed, S12 is executed again.

After S15 is executed, it is determined whether or not the count value ϕ8a has reached the specified number of times ϕ5 (S16). As a result of executing S16, when the count value ϕ8a of switching is determined to have reached the specified number of times ϕ5 (S16: YES), an operation of ending the measurement operation and calculating the moisture content ϕ9 is performed (S23, S24, S25). S23, S24, and S25 will be described later. As a result of executing S21, when the count value ϕ8a of switching is determined to have not reached the specified number of times ϕ5 (S16: NO), acquisition of the first temperature change amount ϕ2 is executed (S17).

Next, it is determined whether or not the first temperature change amount ϕ2 has reached the lower threshold value ϕ4L (S18). As a result of executing S18, when the first temperature change amount ϕ2 is determined to have reached the lower threshold value ϕ4L (S18: YES), a direction of the current is switched (S19). When the direction of the current is switched, the operation of the first heat input/output surface 11a is switched from cooling to heating. After S19 is executed, the count value of the switching operation is updated (S21). As a result of executing S18, when the first temperature change amount ϕ2 is determined to have not reached the lower threshold value ϕ4L (S18: NO), the direction of the current is not switched. Then, after a predetermined period of time has elapsed, S17 is executed again.

After S21 is executed, it is determined whether or not the count value ϕ8a of switching has reached the specified number of times ϕ5 (S22). As a result of executing S22, when the count value ϕ8a of switching is determined to have reached the specified number of times ϕ5 (S22: YES), the operation of ending the measurement operation and calculating the moisture content ϕ9 is performed (S23, S24, S25). As a result of executing S22, when the count value ϕ8a of switching is determined to have not reached the specified number of times ϕ5 (S22: NO), after a predetermined period of time has elapsed, the processing is executed again sequentially from S12.

The operation of ending the measurement operation and calculating the moisture content ϕ9 will be described. First, supply of current is stopped (S23). Next, the elapsed time ϕ8b is obtained (S24). S24 is executed by the switching count unit 41c. Then, the elapsed time ϕ8b is converted into the moisture content ϕ9 (S25).

Operation and Effects of Second Embodiment

Similarly to the soil moisture sensor 1, the soil moisture sensor 1A can obtain stable measurement results.

The soil moisture sensor 1A described above obtains the moisture content ϕ9 using the elapsed time ϕ8b obtained as a result of performing the switching operation a plurality of times. When the result of performing the switching operation a plurality of times is used, it is possible to suppress an influence of variations in the time required for each heating or cooling.

Further, in the second embodiment, whether or not to end the measurement has been determined depending on whether or not the count value ϕ8a of switching has reached the specified number of times ϕ5. Further conditions may be added when determining whether or not to end the measurement. For example, the switching control unit 41A further continues heating or cooling when the count value ϕ8a of switching is determined to have reached the specified number of times ϕ5. Then, the switching control unit 41A may stop supply of the current to the thermoelectric element 11 when the first temperature change amount ϕ2 is determined to have satisfied a predetermined condition.

Such an operation may be performed by an end determination unit 41d shown in FIG. 8. The end determination unit 41d is an additional element and may be provided as necessary. The end determination unit 41d receives the first temperature change amount ϕ2. The end determination unit 41d outputs a signal ϕ10 for stopping an output of the current to the power supply device 50A when conditions are satisfied.

In a case in which the first temperature change amount ϕ2 is determined to be zero, the end determination unit 41d outputs a signal ϕ10 to the power supply device 50A to cause supply of the current to the thermoelectric element 11 to be stopped. "The case in which it can be determined that the first temperature change amount ϕ2 is zero" is not limited to a case in which the first temperature change amount ϕ2 is exactly zero. For example, the end determination unit 41d is configured to set a predetermined allowable range with zero as a reference. Then, the end determination unit 41d may determine that the first temperature change amount ϕ2 is zero when it can be determined that the first temperature change amount ϕ2 is included within the allowable range.

Third Embodiment

For example, the soil moisture sensor 1A may be used in precision agriculture. When the soil moisture sensor 1A is used for precision agriculture, roots of agricultural crops may be present in the soil 100 in the vicinity of the soil moisture sensor 1A. A temperature of the soil 100 affects a quality of agricultural crops. Therefore, when the soil moisture sensor 1A is used for precision agriculture, a difference between the temperature of the soil 100 before measurement and the temperature of the soil 100 after measurement is desired to be made small.

Figure 11:
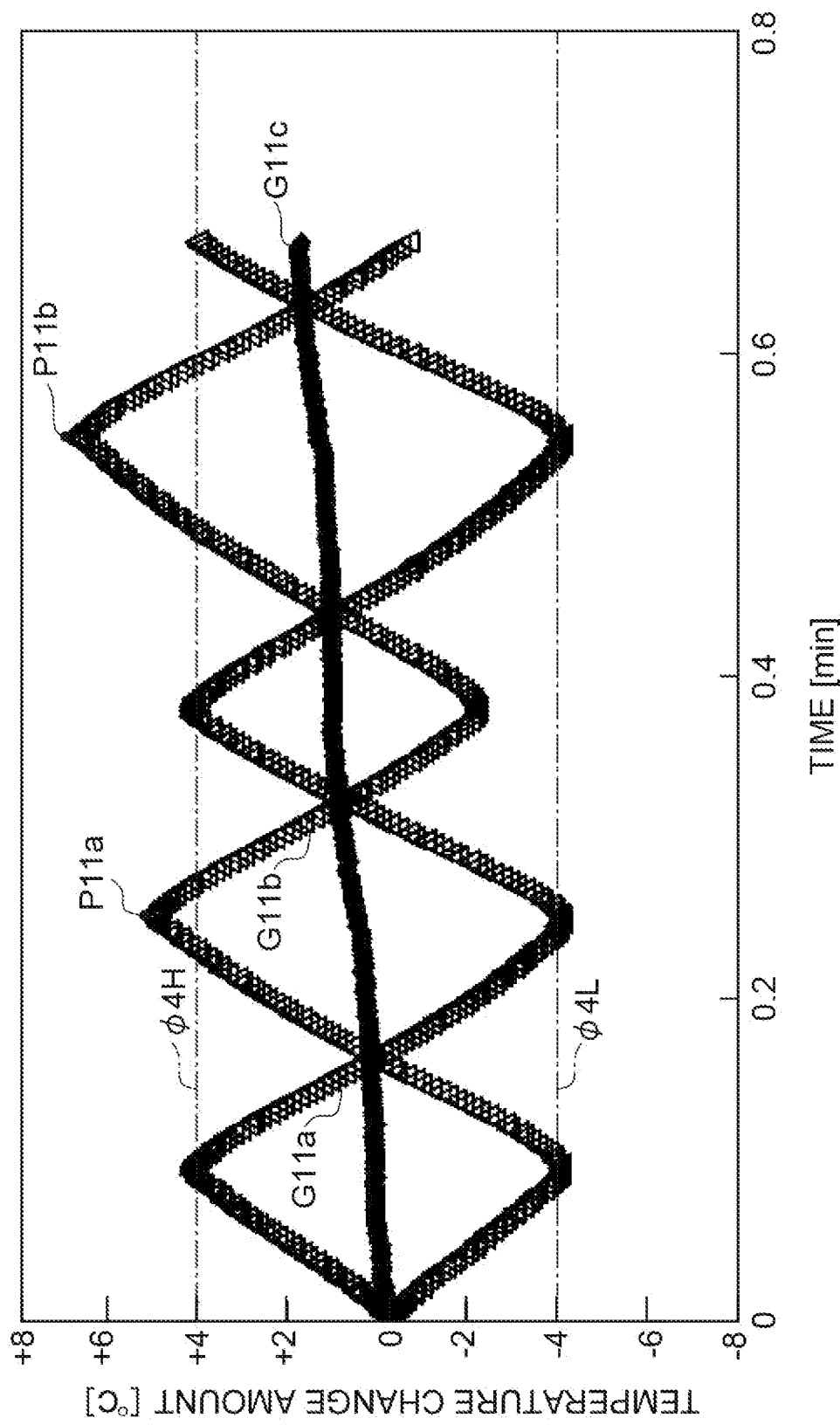
FIG. 11 shows histories of a first temperature and a second temperature when the threshold value is made constant.

As a factor that causes the temperature of the soil 100 to be changed before and after the measurement, Joule heat of the thermoelectric element 11 can be exemplified. FIG. 11 shows the first temperature change amount $\phi2$ (graph G11$a$) and the second temperature change amount $\theta2$ (graph G11$b$) in a case in which heating is switched to cooling when the first temperature change amount $\phi2$ has reached the upper threshold value $\phi4H$ and a case in which cooling is switched to heating when the first temperature change amount $\phi2$ has reached the lower threshold value $\phi4L$. The graph G11$a$ and the graph G11$b$ are actual measured values. In FIG. 11, a graph G11$c$ is a difference between the first temperature change amount $\phi2$ and the second temperature change amount $\theta2$. The difference indicates a temperature due to the Joule heat.

It is necessary to focus on the first temperature change amount $\phi2$ (graph G11$a$). Since the first temperature change amount $\phi2$ is an object of control, it does not greatly deviate from the upper threshold value $\phi4H$ and the lower threshold value $\phi4L$. On the other hand, the second temperature change amount $\theta2$ (graph G11$b$) gradually increases in extreme values (see P11$a$ and P11$b$ in FIG. 11) during heating each time heating and cooling are repeated. As a result, the second temperature change amount $\theta2$ may become higher than the upper threshold value $\phi4H$.

The phenomenon that the extreme values P11$a$ and P11$b$ of the second temperature change amount $\theta2$ gradually increase can be explained by Joule heat generated by the thermoelectric element 11.

For example, a case in which heat is released from the first heat input/output surface 11$a$ and heat is absorbed by the second heat input/output surface 11$b$ is assumed. When a current is supplied to the thermoelectric element 11, heat based on the Peltier effect is released from the first heat input/output surface 11$a$. Further, when a current is supplied to the thermoelectric element 11, Joule heat based on the current is generated. The Joule heat is released from the first heat input/output surface 11$a$. That is, the first heat input/output surface 11$a$ releases heat based on the Peltier effect, and Joule heat.

On the other hand, when a current is supplied to the thermoelectric element 11, heat based on the Peltier effect is absorbed by the second heat input/output surface 11$b$. However, Joule heat is also released from the second heat input/output surface 11$b$. That is, a difference between the heat absorbed on the basis of the Peltier effect and the Joule heat is the heat actually absorbed by the second heat input/output surface 11$b$.

Similarly to the above, a case in which heat is released from the first heat input/output surface 11$a$ and heat is absorbed by the second heat input/output surface 11$b$ is assumed. Since Joule heat is also released from the first heat input/output surface 11$a$ in addition to the heat based on the Peltier effect, the upper threshold value $\phi4H$ is reached in a short period of time. When the first temperature change amount $\phi2$ reaches the upper threshold value $\phi4H$, the second temperature change amount $\theta2$ does not reach the lower threshold value $\phi4L$. This is because the second heat input/output surface 11$b$ releases the Joule heat while heat is absorbed by the Peltier effect.

Then, it is assumed that the switching occurs when heat is absorbed by the first heat input/output surface 11$a$ and heat is released from the second heat input/output surface 11$b$. On the first heat input/output surface 11$a$, absorption of the heat based on the Peltier effect is performed while receiving release of the Joule heat. Therefore, it takes a considerable amount of time for the first temperature change amount $\phi2$ to reach the lower threshold value $\phi4L$. On the other hand, on the second heat input/output surface 11$b$, release of the Joule heat is also performed in addition to heat release based on the Peltier effect. Therefore, since an amount of heat released increases, the temperature of the soil 100 on the second heat input/output surface 11$b$ side tends to increase.

Therefore, the extreme value of the second temperature change amount $\theta2$, which is not an object to be controlled, increases each time heating and cooling are repeated.

A soil moisture sensor 1B to be described next realizes an operation in which an extreme value of the second temperature change amount $\theta2$, which is not an object to be controlled, does not exceed the upper threshold value $\phi4H$. As a result, the soil moisture sensor 1B can reduce a difference between a temperature of the soil 100 before measurement and a temperature of the soil 100 after measurement.

In the soil moisture sensor 1A of the second embodiment, the upper threshold value $\phi4H$ was a constant value. That is, the upper threshold value $\phi4H$ was one value. The same applies to the lower threshold value $\phi4L$. In contrast, the soil moisture sensor 1B employs a plurality of upper threshold values $\phi4Ha$, $\phi4Hb$, and $\phi4Hc$ different from each other. Further, the soil moisture sensor 1B employs a plurality of lower threshold values $\phi4La$ and $\phi4Lb$ different from each other.

Figure 12:
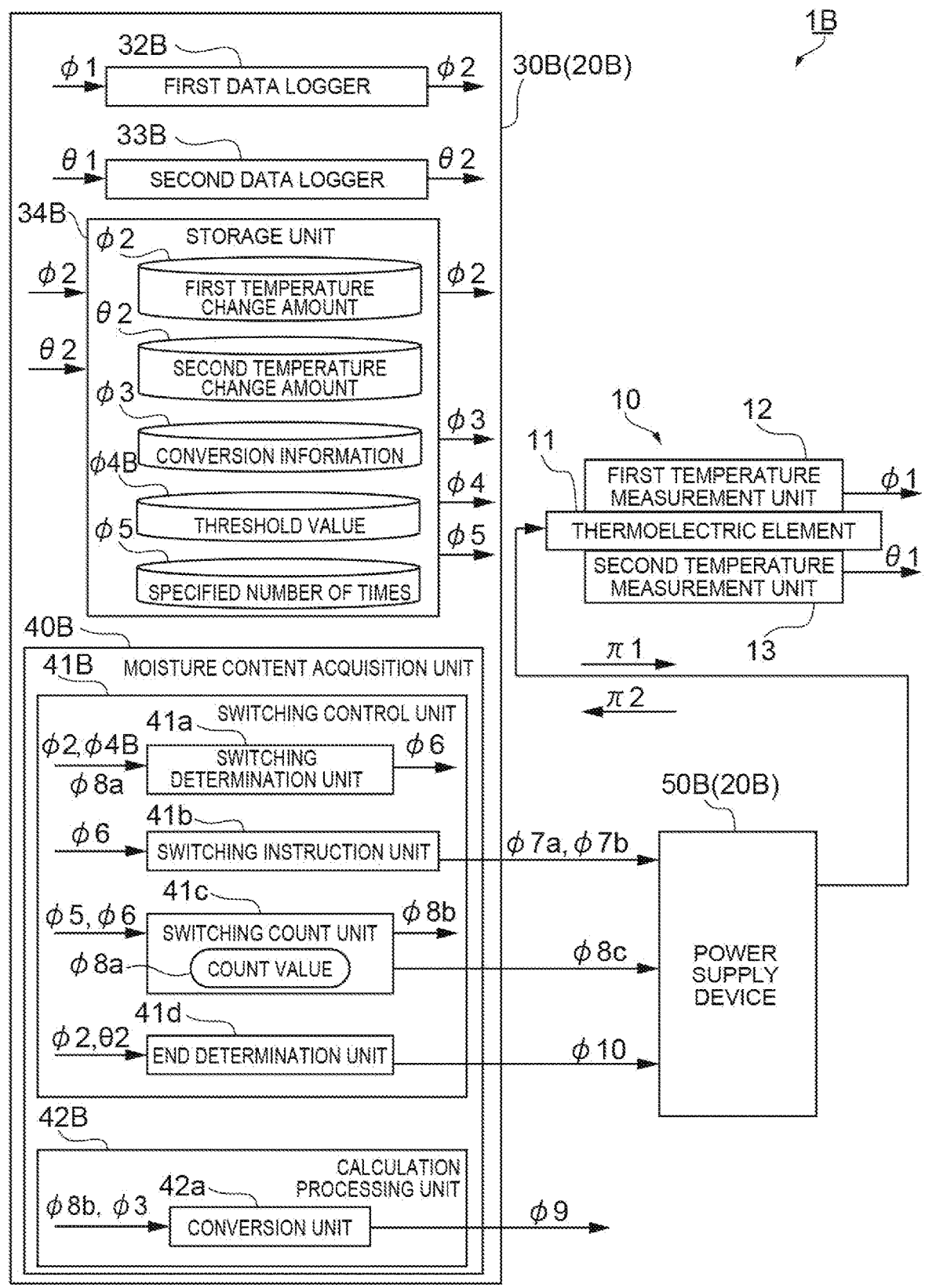
FIG. 12 is a diagram showing a configuration of a moisture sensor of a third embodiment in detail.

As shown in FIG. 12, the soil moisture sensor 1B includes a sensor unit 10 and a control unit 20B. The sensor unit 10 is the same as the sensor unit 10 of the soil moisture sensor 1 in the first embodiment. Therefore, detailed description of the sensor unit 10 will be omitted. The control unit 20B includes an arithmetic device 30B and a power supply device 50B. The power supply device 50B is the same as the power supply device 50A of the soil moisture sensor 1A. Therefore, detailed description of the power supply device 50B will be omitted.

The arithmetic device 30B includes a first data logger 32B, a second data logger 33B, a storage unit 34B, and a moisture content acquisition unit 40B. The first data logger 32B and the second data logger 33B are the same as the first data logger 32A and the second data logger 33A of the soil moisture sensor 1A. Therefore, detailed description of the first data logger 32B and the second data logger 33B will be omitted.

The storage unit 34B stores a first temperature change amount $\phi2$, a second temperature change amount $\theta2$, conversion information $\phi3$, and a specified number of times $\phi5$. The storage unit 34B further stores a threshold value $\phi1B$. The moisture content acquisition unit 40B includes a switching control unit 41B and a calculation processing unit 42B.

Figure 13:
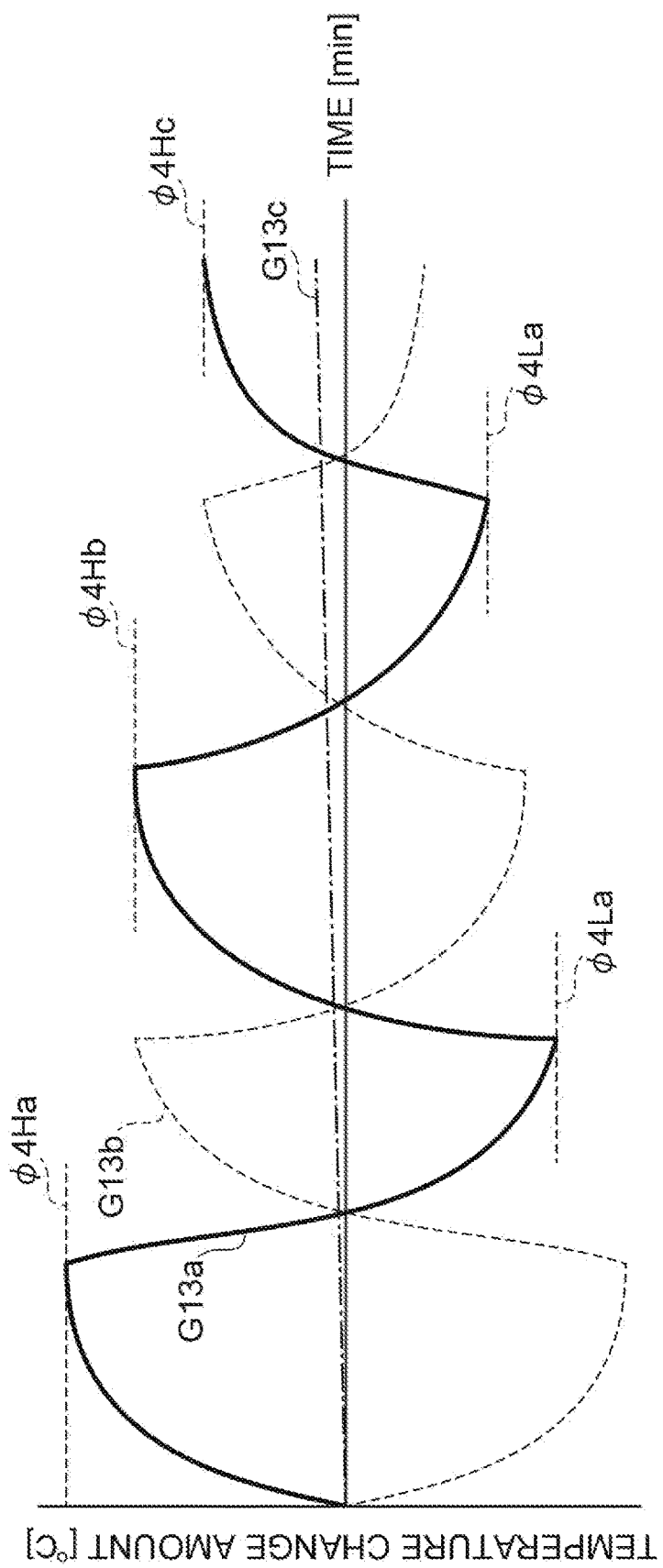
FIG. 13 shows histories of a first temperature and a second temperature when the threshold value is made variable.

As shown in FIG. 13, the threshold value $\phi4B$ includes a plurality of upper threshold values $\phi4Ha$, $\phi4Hb$, and $\phi4Hc$. In the present embodiment, three upper threshold values are exemplified, but the number of upper threshold values may be appropriately set according to the specified number of times $\phi5$ of the switching operation. Information indicating that the upper threshold values $\phi4Ha$, $\phi4Hb$, and $\phi4Hc$ are each used for an n-th (n is an integer of 1 or more and N or less) heating operation is also contained in the reference signs. For example, the upper threshold value $\phi4Ha$ is used for a first heating operation. The upper threshold value $\phi4Hb$ is used for a second heating operation. The upper threshold value $\phi4Hc$ is used for a third heating operation.

The threshold values $\phi4B$ further includes a plurality of lower threshold values $\phi4La$ and $\phi4Lb$. In the present embodiment, three lower threshold values are exemplified, but the number of lower threshold values may be appropriately set according to the specified number of times $\phi5$ of the switching operation. Information indicating that the lower threshold values φ4La and φ4Lb are each used for an n-th (n is an integer of 1 or more and N or less) cooling operation is also contained in the reference signs. For example, the lower threshold value φ4La is used for a first cooling operation. The lower threshold value φ4Lb is used for a second cooling operation.

Heating and cooling are alternately performed. Therefore, the above-described five threshold values are used in an order of the upper threshold value φ4Ha, the lower threshold value φ4La, the upper threshold value φ4Hb, the lower threshold value φ4Lb, and the upper threshold value φ4Hc.

A provision that the threshold values are different can be rephrased as that absolute values of the threshold values are different. The above-described five threshold values are set so that the absolute values gradually decrease.

More specifically, an absolute value of the lower threshold value φ4La used after the upper threshold value φ4Ha is smaller than an absolute value of the upper threshold value φ4Ha. That is, in repeating heating and cooling, an absolute value of the threshold value used at the time of cooling is smaller than an absolute value of the threshold value that has been used for heating performed immediately before the cooling. The upper threshold value φ4Ha may, as an example, be +4 degrees, and the lower threshold value φ4La may, as an example, be −3 degrees.

In contrast, an absolute value of the upper threshold value φ4Hb used after the lower threshold value φ4La may be the same as the absolute value of the lower threshold value φ4La. That is, in repeating heating and cooling, an absolute value of the threshold value used at the time of heating may be set to be the same as an absolute value of the threshold value that has been used for cooling performed immediately before the heating. The lower threshold value φ4La may, as an example, be −3 degrees, and the upper threshold value φ4Hb may, as an example, be +3 degrees.

In summary, the plurality of threshold values may be set as follows.

Upper threshold value φ4Ha: +4 degrees.
Lower threshold value φ4La: −3 degrees.
Upper threshold value φ4Hb: +3 degrees.
Lower threshold value φ4Lb: −2 degrees.
Upper threshold value φ4Hc: +2 degrees.

The switching determination unit 41a determines whether or not to switch between heating and cooling using five threshold values and a count value φ8a. The count value φ8a may be used to control which of the five threshold values to use for the first temperature change amount φ2.

Operations of a switching instruction unit 41b and a switching count unit 41c are the same as those of the second embodiment, and detailed description thereof will be omitted. Further, an operation of the calculation processing unit 42 is also the same as that of the second embodiment, and detailed description thereof will be omitted.

<Operation Flow of Soil Moisture Sensor of Third Embodiment>

FIG. 14 shows an operation flow of the soil moisture sensor 1B of the third embodiment. A difference from the operation flow of the second embodiment is that an operation of changing the threshold value (S15a, S21a) is added after the count value φ8a is updated (S15, S21). Since the other steps are the same as those in the operation flow of the second embodiment, detailed description thereof will be omitted.

Operation and Effects of Third Embodiment

Similarly to the soil moisture sensor 1, the above-described soil moisture sensor 1B can obtain stable measurement results.

The soil moisture sensor 1B reduces the absolute value of the threshold value each time heating and cooling are repeated. As a result, the second temperature change amount θ2 of the second heat input/output surface 11b, which is not an object to be controlled, does not exceed the highest upper threshold value φ4Ha.

Further, the soil moisture sensor 1B reduces the absolute value of the threshold value each time heating and cooling are repeated. According to this operation, a time until reaching the threshold value is gradually shortened each time heating and cooling are repeated. As a result, an elapsed time φ8b until reaching the specified number of times φ5 can be shortened. Joule heat is proportional to a time during which a current flows. Therefore, a total amount of Joule heat generated by the thermoelectric element 11 during the measurement operation can be suppressed. Therefore, through the above-described two actions, the soil moisture sensor 1B can suitably maintain a temperature state of the soil 100 which is a measurement object.

Further, also in the third embodiment, as in the second embodiment, whether or not to end the measurement has been determined depending on whether or not the count value φ8a of switching has reached the specified number of times φ5. Further conditions may be added when determining whether or not to end the measurement. For example, the switching control unit 41B further continues heating or cooling when the count value φ8a of switching is determined to have reached the specified number of times φ5. Then, the switching control unit 41B may stop supply of the current to the thermoelectric element 11 when the first temperature change amount φ2 and the second temperature change amount θ2 are determined to have satisfied a predetermined condition.

Such an operation may be performed by the end determination unit 41d shown in FIG. 12. The end determination unit 41d receives the first temperature change amount φ2 and the second temperature change amount θ2. For example, in a case in which the first temperature change amount φ2 and the second temperature change amount θ2 have been determined to coincide with each other, the end determination unit 41d outputs a signal φ10, which causes supply of the current to the thermoelectric element 11 to be stopped, to the power supply device 50B. "The case in which it can be determined that the first temperature change amount φ2 and the second temperature change amount θ2 coincide with each other" is not limited to a case in which the first temperature change amount φ2 and the second temperature change amount θ2 exactly coincide with each other. For example, the end determination unit 41d obtains a difference between the first temperature change amount φ2 and the second temperature change amount θ2. "The case in which the first temperature change amount φ2 and the second temperature change amount θ2 exactly coincide with each other" is that the difference is zero. When the difference is zero, the first temperature change amount φ2 and the second temperature change amount θ2 may be determined to coincide with each other. Further, the end determination unit 41d is configured to set a predetermined allowable range with zero as a reference. Then, when it can be determined that the difference between the first temperature change amount φ2 and the second temperature change amount θ2 is included in the allowable range, the end determination unit 41d may determine that the first temperature change amount φ2 and the second temperature change amount θ2 have coincided with each other.

Experimental Example 1 of Soil Moisture Sensor
of Third Embodiment

An experiment for ascertaining effects of the soil moisture sensor 1B was performed. In this experiment, it was ascertained that the soil moisture sensor 1B could control so that the temperature change amount, which is not an object to be controlled, did not deviate from the threshold value. Experimental conditions are as follows.

An absolute value of a voltage applied to the thermoelectric element: 1.3V.
Upper threshold value φ4Ha: +4 degrees.
Lower threshold value φ4La: −3 degrees.
Upper threshold value φ4Hb: +3 degrees.
Lower threshold value φ4Lb: −2 degrees.
Upper threshold value φ4Hc: +2 degrees.
Measurement object: simulated soil with the moisture content of 0%.

FIG. 15(a) shows temperature histories of the first temperature change amount φ2 and the second temperature change amount θ2. The horizontal axis represents a measurement time. The vertical axis represents a temperature change amount from the reference temperature TS. A graph G15a indicates the first temperature change amount φ2. A graph G15b indicates the second temperature change amount θ2. The graph G15a and the graph G15b are actual measured values. A graph G15c indicates a temperature due to the Joule heat. The temperature due to the Joule heat is the difference between the first temperature change amount φ2 and the second temperature change amount θ2. Therefore, the graph G15c is a calculated value.

The first temperature change amount φ2 (graph G15a) is an object to be controlled. Therefore, the first temperature change amount φ2 (graph G15a) did not exceed the upper threshold value φ4Ha. The second temperature change amount θ2 (graph G15b) is not an object to be controlled. However, the second temperature change amount θ2 also did not exceed the upper threshold value φ4Ha by changing the threshold value. Therefore, it was found that the soil moisture sensor 1B could control so that the temperature change amount, which is not an object to be controlled, did not deviate from the threshold value.

Experimental Example 2 of Soil Moisture Sensor
of Third Embodiment

Another experiment (experimental example 2) for ascertaining effects of the soil moisture sensor 1B was performed. In this experiment, it was ascertained that the soil moisture sensor 1B could suppress the temperature rise due to the Joule heat at the end of the measurement. Experimental conditions are as follows.

An absolute value of a voltage applied to the thermoelectric element: 1.3V.
Upper threshold value φ4Ha: +4 degrees.
Lower threshold value φ4La: −3 degrees.
Upper threshold value φ4Hb: +3 degrees.
Lower threshold value φ4Lb: −2 degrees.
Upper threshold value φ4Hc: +2 degrees.
Measurement object (A): Simulated soil with the moisture content of 0%.
Measurement object (B): simulated soil with the moisture content of 10%.
Measurement object (C): Simulated soil with the moisture content of 30%.
Measurement object (D): Simulated soil with the moisture content of 50%.

Further, as a comparative example, an experiment according to the following conditions was also performed.
An absolute value of a voltage applied to the thermoelectric element: 3V.
Upper threshold value φ4H: +4 degrees.
Lower threshold value φ4L: −4 degrees.
Measurement object (A): Simulated soil with the moisture content of 0%.
Measurement object (B): simulated soil with the moisture content of 10%.
Measurement object (C): Simulated soil with the moisture content of 30%.
Measurement object (D): Simulated soil with the moisture content of 50%.

The horizontal axis of the graph in FIG. 15(b) represents a moisture content. The vertical axis of the graph in FIG. 15(b) represents a temperature TJ increased due to the Joule heat. A graph G15d shows results of experimental example 2. A graph G15e shows results of the comparative example.

Referring to the graph G15e, which is the comparative example, it was found that the temperature TJ was higher than +1 degrees regardless of the moisture content. On the other hand, referring to the graph G15d of experimental example 2, it was found that the temperature TJ was lower than +1 degrees regardless of the moisture content. Therefore, it was found that the soil moisture sensor 1B could suppress the temperature rise due to the Joule heat at the end of the measurement.

Experimental Example 3 of Soil Moisture Sensor
of Third Embodiment

Another experiment (experimental example 3) for ascertaining effects of the soil moisture sensor 1B was performed. In this experiment, it was ascertained that the soil moisture sensor 1C could improve a resolution for measuring the moisture content. Experimental conditions are the same as those in experimental example 2.

The horizontal axis of FIG. 16(a) represents a moisture content. The vertical axis of FIG. 16(b) represents a time until a threshold value is reached. The "time until the threshold value is reached" is, in other words, the elapsed time φ8b.

Referring to the graph G16b serving as the comparative example, it was found that a difference between a threshold value reaching time when the moisture content was 0% and a threshold value reaching time when the moisture content was 50% was about 0.1 minute (6 seconds). In contrast, referring to the graph G16a serving as experimental example 3, it was found that a difference between the threshold value reaching time when the moisture content was 0% and a threshold value reaching time when the moisture content was 50% was about 0.4 minute (24 seconds). The difference being large indicates that there is a large difference in the threshold value reaching time with respect to the difference in the moisture content. That is, even a slight difference in the moisture content can be regarded as a large change in the threshold value reaching time. Therefore, it was found that the soil moisture sensor 1B could improve the resolution for measuring the moisture content.

Experimental Example 4 of Soil Moisture Sensor
of Third Embodiment

Another experiment (experimental example 4) for ascertaining effects of the soil moisture sensor 1B was performed. In this experiment, it was ascertained that a resolution of the moisture content could be improved even by increasing the number of times of switching between heating and cooling. Experimental conditions are as follows.

Absolute value of the voltage applied to the thermoelectric element: 1.3V.
Upper threshold value ϕ4Ha: +4 degrees.
Lower threshold value ϕ4La: −3 degrees.
Upper threshold value ϕ4Hb: +3 degrees.
Lower threshold value ϕ4Lb: −2 degrees.
Upper threshold value ϕ4Hc: +2 degrees.
Measurement object (A): Simulated soil with the moisture content of 0%.
Measurement object (D): Simulated soil with the moisture content of 50%.
The horizontal axis of FIG. 16(b) represents a measurement time. The vertical axis of FIG. 16(b) represents a temperature change amount. A graph G16c is a history of a temperature change amount in the simulated soil with the moisture content of 0%. A graph G16d is a history of a temperature change amount in the simulated soil with the moisture content of 50%.

First, in a first heating, it was found that a difference (Δt1) in time until the upper threshold value ϕ4Ha was reached was 0.12 minutes. Then, in a third heating, it was found that a difference (Δt2) in time until the upper threshold value ϕ4Ha was reached was 0.42 minutes. That is, it was found that a difference in time until a specified number of times was reached could be increased by increasing the number of times of switching between heating and cooling in one measurement operation. Therefore, it was found that a resolution of the moisture content could also be improved by increasing the number of times of switching between heating and cooling.

Fourth Embodiment

The soil moisture sensor 1A of the second embodiment employed temperature as the switching condition for alternately switching between heating and cooling. Then, the soil moisture sensor 1A obtained the moisture content by using the time required for switching between heating and cooling a specified number of times. A soil moisture sensor 1C of a fourth embodiment employs time as a switching condition. Then, the soil moisture sensor 1C obtains a moisture content by using extreme values of temperature caused by heating and cooling.

Figure 17:
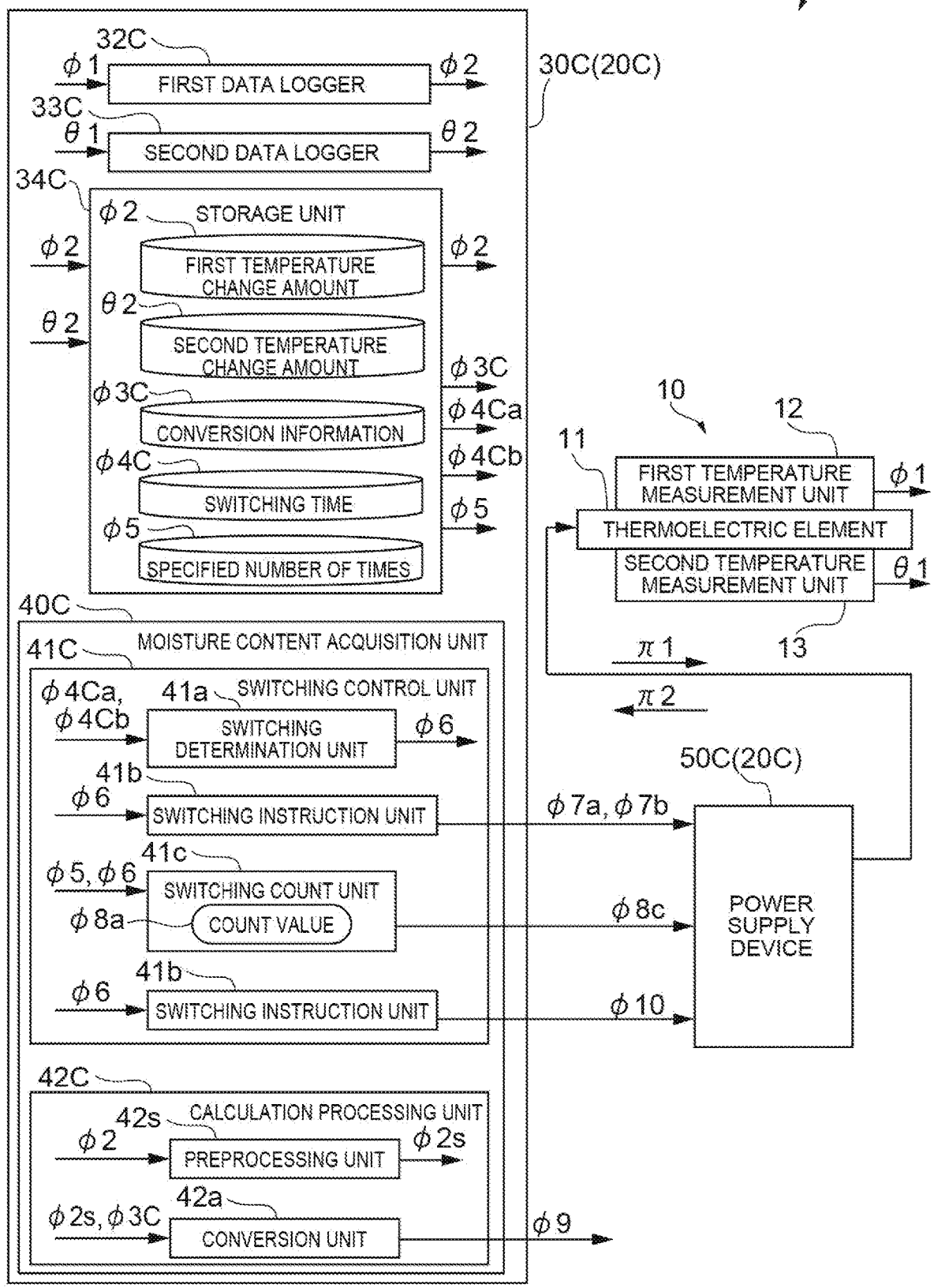
FIG. 17 is a diagram showing a configuration of a moisture sensor of a fourth embodiment in detail.

As shown in FIG. 17, the soil moisture sensor 1C includes a sensor unit 10 and a control unit 20C. The sensor unit 10 is the same as the sensor unit 10 of the soil moisture sensor 1 in the first embodiment. Therefore, detailed description of the sensor unit 10 will be omitted. Then, the control unit 20C includes an arithmetic device 30C and a power supply device 50C. The power supply device 50C is the same as the power supply device 50A of the soil moisture sensor 1A. Therefore, detailed description of the power supply device 50C will be omitted.

The arithmetic device 30C includes a first data logger 32C, a second data logger 33C, a storage unit 34C, and a moisture content acquisition unit 40C. The first data logger 32C and the second data logger 33C are the same as the first data logger 32A and the second data logger 33A of the soil moisture sensor 1A. Therefore, detailed description of the first data logger 32C and the second data logger 33C will be omitted.

The storage unit 34C stores a first temperature change amount ϕ2, a second temperature change amount θ2, conversion information ϕ3C, and a specified number of times ϕ5. The storage unit 34B further stores a switching time ϕ4C. The switching time ϕ4C includes a heating maintenance time ϕ4Ca and a cooling maintenance time ϕ4Cb. In the following description, the "heating maintenance time ϕ4Ca" is assumed to be a heating time at a second heat input/output surface 11b. Similarly, the "cooling maintenance time ϕ4Cb" is assumed to be a cooling time at the second heat input/output surface 11b. Further, when the second heat input/output surface 11b is in a state of heating, a first heat input/output surface 11a is in a state of cooling. Therefore, the "heating maintenance time ϕ4Ca" is a cooling maintenance time from the viewpoint of the first heat input/output surface 11a. Similarly, the "cooling maintenance time ϕ4Cb" is a heating maintenance time from the viewpoint of the first heat input/output surface 11a.

The soil moisture sensor 1C converts a temperature change amount into a moisture content. The conversion information ϕ3C includes information for converting the temperature change amount into the moisture content. The conversion information ϕ3C may be, for example, a function in which the temperature change amount is used as an independent variable and the moisture content is used as a dependent variable.

For example, during a period in which heating and cooling are repeated, the soil moisture sensor 1C starts heating of the second heat input/output surface 11b and then switches to cooling when the heating maintenance time ϕ4Ca has elapsed. The soil moisture sensor 1C starts cooling of the second heat input/output surface 11b and then switches to heating when the cooling maintenance time ϕ4Cb has elapsed.

The moisture content acquisition unit 40C includes a switching control unit 41C and a calculation processing unit 42C. The switching control unit 41C obtains control signals ϕ7a and ϕ7b to be provided to the power supply device 50C by using the heating maintenance time ϕ4Ca and the cooling maintenance time ϕ4Cb. The calculation processing unit 42C obtains a moisture content ϕ9 by using the first temperature change amount ϕ2 or the second temperature change amount θ2.

A switching determination unit 41a of the switching control unit 41C receives the heating maintenance time ϕ4Ca and the cooling maintenance time ϕ4Cb. The switching determination unit 41a determines whether or not an elapsed time has reached the heating maintenance time ϕ4Ca at a predetermined timing during execution of the heating operation of the second heat input/output surface 11b. Similarly, the switching determination unit 41a determines whether or not an elapsed time has reached the cooling maintenance time ϕ4Cb at a predetermined timing during execution of the cooling operation of the second heat input/output surface 11b. The switching determination unit 41a outputs a determination result 46 when the elapsed time reaches the heating maintenance time ϕ4Ca or when the elapsed time reaches the cooling maintenance time ϕ4Cb.

The switching instruction unit 41b and the switching count unit 41c are the same as those in the second embodiment, and detailed description thereof will be omitted. Further, the soil moisture sensor 1C does not utilize the elapsed time ϕ8b to obtain the moisture content. Therefore, the switching count unit 41c of the soil moisture sensor 1C may not output the elapsed time ϕ8b.

The calculation processing unit 42C includes a preprocessing unit 42s and a conversion unit 42a. The preprocessing unit 42s receives the first temperature change amount ϕ2. The preprocessing unit 42s obtains a preprocessed value ϕ2s using the first temperature change amount ϕ2. The preprocessing unit 42s outputs the preprocessed value $\phi 2s$ to the conversion unit 42a. The conversion unit 42a receives the preprocessed value $\phi 2s$ and the conversion information $\phi 3C$. The conversion unit 42a converts the preprocessed value $\phi 2s$ into the moisture content $\phi 9$ using the conversion information $\phi 3C$.

Figure 18:
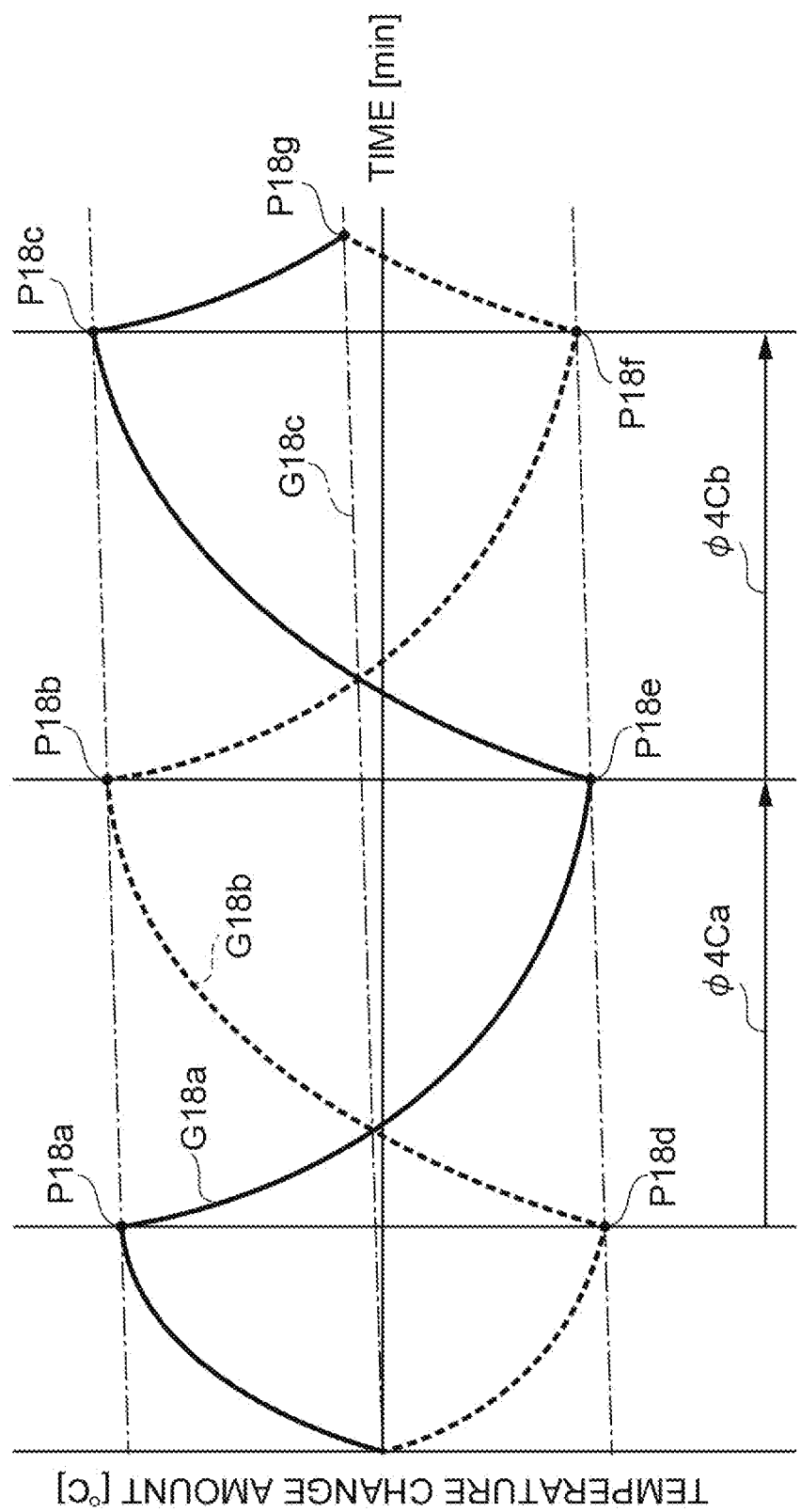
FIG. 18 shows histories of a first temperature and a second temperature obtained by an operation of switching between heating and cooling at predetermined times.

Here, the preprocessed value $\phi 2s$ will be described. The preprocessed value $\phi 2s$ is a temperature change amount. FIG. 18 shows a temporal change of the temperature change amount when heating and cooling are switched each time a certain period of time elapses. The horizontal axis of FIG. 18 represents a time. The vertical axis of FIG. 18 represents a temperature change amount. A graph G18a indicates the first temperature change amount $\phi 2$. A graph G18b indicates the second temperature change amount $\theta 2$.

Referring to the graphs G18a and G18b, there are extreme values P18a, P18b, and P18c on a high temperature side. The extreme values P18a and P18c of the graph G18a are temperatures of the first heat input/output surface 11a. The extreme value P18b of the graph G18b is a temperature of the second heat input/output surface 11b. For example, of the extreme values P18a, P18b, and P18c, a highest extreme value P18c may be used as the preprocessed value $\phi 2s$. Also, a total value obtained by summing all the extreme values P18a, P18b, and P18c may be used as the preprocessed value $\phi 2s$. Further, an average value of the extreme values P18a, P18b, and P18c may be used as the preprocessed value $\phi 2s$.

The preprocessed value $\phi 2s$ may be a value based on extreme values P18d, P18e, and P18f on a low temperature side present in the graph G18a and the graph G18b. The extreme value P18e of the graph G18a is a temperature of the first heat input/output surface 11a. The extreme values P18d and P18f of the graph G18b are temperatures of the second heat input/output surface 11b. For example, of the extreme values P18d, P18e, and P18f, a lowest extreme value P18d may be used as the preprocessed value $\phi 2s$. Also, a total value obtained by summing all the extreme values P18d, P18e, and P18f may be used as the preprocessed value $\phi 2s$. Further, an average value of the extreme values P18d, P18e, and P18f may be used as the preprocessed value $\phi 2s$.

Further, the preprocessed value $\phi 2s$ may be a value obtained as a difference between the first temperature change amount $\phi 2$ and the second temperature change amount $\theta 2$. In FIG. 18, the difference is indicated as a graph G18c.

<Operation Flow of Soil Moisture Sensor of Fourth Embodiment>

FIG. 19 shows an operation flow of the soil moisture sensor 1C of the fourth embodiment. First, the heating maintenance time $\phi 4Ca$ is set (S51). Next, a cooling maintenance time $\phi 4Cb$ is set (S52). Next, supply of a current is started (S53). Counting of an elapsed heating time is also started at the same time as supply of the current is started.

Next, it is determined whether or not the elapsed heating time has reached the heating maintenance time $\phi 4Ca$ (S54). If the elapsed heating time is determined to have not reached the heating maintenance time $\phi 4Ca$ (S54: NO), S54 is executed again after elapse of a predetermined time. If the elapsed heating time is determined to have reached the heating maintenance time $\phi 4Ca$ (S54: YES), a direction of the current is switched (S55). When the direction of the current is switched, counting of an elapsed cooling time starts as a new elapsed time. Next, the count value $\phi 8a$ of switching is updated (S56). Next, it is determined whether or not the number of times of switching has reached the specified number of times $\phi 5$ (S57). If the number of times of switching is determined to have reached the specified number of times 45 (S57: YES), the processing proceeds to processing of obtaining the moisture content (S63, S64, S65).

If the number of times of switching is determined to have not reached the specified number of times $\phi 5$ (S57: NO), it is determined whether or not the elapsed cooling time has reached the cooling maintenance time $\phi 4Cb$ (S54). If the elapsed cooling time is determined to have not reached the cooling maintenance time $\phi 4Cb$ (S58: NO), S58 is executed again after elapse of a predetermined time. If the elapsed cooling time is determined to have reached the cooling maintenance time $\phi 4Cb$ (S58: YES), a direction of the current is switched (S59). When the direction of the current is switched, counting of the elapsed heating time starts as a new elapsed time.

Next, the count value $\phi 8a$ of switching is updated (S61). Next, it is determined whether or not the number of times of switching has reached the specified number of times $\phi 5$ (S62). If the number of times of switching is determined to have reached the specified number of times 45 (S62: YES), the processing proceeds to processing of obtaining the moisture content (S63, S64, S65). If the number of times of switching is determined to have not reached the specified number of times $\phi 5$ (S62: NO), it is determined again whether or not the elapsed heating time has reached the heating maintenance time $\phi 4Ca$ (S54).

In the processing of obtaining the moisture content $\phi 9$, supply of the current is first stopped (S63). Next, the preprocessed value $\phi 2s$ is obtained. Then, the preprocessed value $\phi 2s$ is converted into the moisture content $\phi 9$ (S65).

Further, in the fourth embodiment, the same method as in the third embodiment may be used for determining whether or not to end the measurement. That is, an end determination unit 41d may end the measurement on condition that the first temperature change amount $\phi 2$ coincides with the second temperature change amount $\theta 2$ as indicated by the point P18g in FIG. 18. As described in the third embodiment, "the first temperature change amount $\phi 2$ coinciding with the second temperature change amount $\theta 2$" does not require an exact coincidence. When it can be determined that the difference between the first temperature change amount $\phi 2$ and the second temperature change amount $\theta 2$ is included within an allowable range, it may be determined that the first temperature change amount $\phi 2$ and the second temperature change amount $\theta 2$ coincide with each other.

Operation and Effects of Fourth Embodiment

Similarly to the soil moisture sensor 1, the above-described soil moisture sensor 1C can obtain stable measurement results by obtaining information on the moisture using the temperature change amount caused by specific heat.

The soil moisture sensor 1C switches between heating and cooling each time a predetermined time elapses. The first temperature change amount $\phi 2$ and the second temperature change amount $\theta 2$ (see FIG. 18) obtained by the operation can remove an influence of temperature due to the Joule heat by correction. For example, the extreme values P18a, P18b, and P18c included in the graph G18a of FIG. 18 rise substantially linearly with the elapse of time. This rise is predicted to be due to an influence of the Joule heat. Therefore, an approximate straight line connecting the extreme values P18a, P18b, and P18c is set. Then, a function representing the approximate straight line is obtained. When the first temperature change amount $\phi 2$ is corrected using the function, it is possible to obtain information on a temperature history from which an influence of the Joule heat has been removed.

REFERENCE SIGNS LIST 1, 1A, 1B, 1C Soil moisture sensor
10 Sensor unit
11 Thermoelectric element (temperature control unit)
11a First heat input/output surface
11b Second heat input/output surface
12 First temperature measurement unit
13 Second temperature measurement unit
20, 20A, 20B, 20C Control unit
30, 30A, 30B, 30C Arithmetic device (arithmetic unit)
31 Voltage control unit
32 First data logger
33 Second data logger
34 Storage unit
35 Gradient information acquisition unit
36 Equilibrium temperature acquisition unit
37 Conversion unit
40A, 40B, 40C Moisture content acquisition unit
41A, 41B, 41C Switching control unit
41a Switching determination unit
41b Switching instruction unit
41c Switching count unit
42A, 42B, 42C Calculation processing unit
42a Conversion unit
42s Preprocessing unit
50 Power supply device (power supply unit)
M1 First temperature information acquisition unit
M2 Second temperature information acquisition unit
100 Soil

The invention claimed is:

1. A moisture sensor which obtains moisture information on moisture contained in a measurement object, the moisture sensor comprising:
a temperature control unit disposed in the measurement object and being able to change a temperature of the measurement object;
a temperature information acquisition unit acquiring temperature information indicating a temporal change of the temperature of the measurement object due to an operation of the temperature control unit; and
an arithmetic unit obtaining the moisture information on the basis of the temperature information, wherein
the arithmetic unit includes:
a gradient information acquisition unit acquiring a temperature change amount per unit time by utilizing the temperature information; and
a conversion unit converting the temperature change amount into the moisture information by utilizing conversion information indicating a relationship between the temperature change amount and the moisture information,
the temperature control unit is a thermoelectric element which converts electrical energy into thermal energy,
the thermoelectric element includes a first heat input/output surface and a second heat input/output surface in contact with the measurement object, providing heat to the measurement object, and dissipating heat from the measurement object, and is able to perform an operation of providing heat to the measurement object from one of the first heat input/output surface and the second heat input/output surface and dissipation heat from the measurement object by the other of the first heat input/output surface and the second heat input/output surface,
the temperature information acquisition unit includes a first temperature measurement unit attached to the first heat input/output surface, and a second temperature attached to e second heat input/output surface,
the gradient information acquisition unit acquires a first temperature change amount by utilizing first temperature information obtained from the first temperature measurement unit and acquires a second temperature change amount by utilizing second temperature information obtained from the second temperature measurement unit, and
the conversion unit obtains the moisture information by utilizing the conversion information, the first temperature change amount, and the second temperature change amount.

2. The moisture sensor according to claim 1, wherein the gradient information acquisition unit acquires the temperature change amount using a difference between a first temperature and a second temperature during a transient period in a change of the temperature of the measurement object over time.

3. The moisture sensor according to claim 2, wherein the temperature information acquisition unit is disposed to be in contact with the measurement object.

4. A moisture sensor which obtains moisture information on moisture contained in a measurement object, the moisture sensor comprising:
a thermoelectric element disposed in the measurement object and being able to change a temperature of the measurement object;
a power supply unit supplying a current to the thermoelectric element and being able to switch a direction of the current supplied to the thermoelectric element;
a temperature information acquisition unit acquiring the temperature of the measurement object; and
a moisture content acquisition unit controlling a direction of the current supplied to the thermoelectric element from the power supply unit and acquiring the moisture information by utilizing the temperature acquired by the temperature information acquisition unit, wherein
the moisture temperature content acquisition unit includes a switching control unit which controls a direction of the current supplied to thermoelectric element from the power supply unit by utilizing the temperature measurement object,
the switching control unit performs the switching operation N times (N is an integer of 1 or more), and
the moisture content acquisition unit acquires the moisture information using an elapsed time required for the switching operation of N times.

5. The moisture sensor according to claim 4, wherein the switching control unit performs a switching operation of switching a direction of the current supplied to the thermoelectric element from the power supply unit when the temperature of the measurement object has reached at least one predetermined threshold value.

6. The moisture sensor according to claim 5, wherein the switching control unit controls a direction of the current supplied to the thermoelectric element from the power supply unit by utilizing one predetermined threshold value.

7. The moisture sensor according to claim 5, wherein the switching control unit controls a direction of the current supplied to the thermoelectric element from the power supply unit by utilizing a plurality of predetermined threshold values different from each other.

8. The moisture sensor according to claim 5, wherein an absolute value of the threshold value utilized when the measurement object is cooled is smaller than an absolute value of the threshold value utilized when the measurement object is heated.

9. The moisture sensor according to claim 5, wherein
the thermoelectric element includes a first heat input/output surface and a second heat input/output surface which are in contact with the measurement object and configured to provide heat to the measurement object and dissipate heat from the measurement object,
the temperature information acquisition unit includes a first temperature measurement unit attached to the first heat input/output surface,
the plurality of threshold values include one or more upper threshold values higher than the temperature of the measurement object before a start of measurement and one or more lower threshold values lower than the temperature of the measurement object before the start of measurement, and
the switching control unit switches a direction of the current when a temperature acquired by the first temperature measurement unit has reached the upper threshold value or the lower threshold value.

10. The moisture sensor according to claim 5, wherein
the thermoelectric element includes a first heat input/output surface and a second heat input/output surface which are in contact with the measurement object and configured to provide heat to the measurement object and dissipate heat from the measurement object,
the temperature information acquisition unit includes a first temperature measurement unit attached to the first heat input/output surface, and a second temperature measurement unit attached to the second heat input/output surface,
the plurality of threshold values include one or more upper threshold values higher than the temperature of the measurement object before a start of measurement, and
the switching control unit switches a direction of the current when a temperature acquired by the first temperature measurement unit has reached the upper threshold value or when a temperature acquired by the second temperature measurement unit has reached the upper threshold value.

11. The moisture sensor according to claim 10, wherein
the temperature information acquisition unit acquires the temperature of the measurement object before the start of measurement as a reference temperature, and
the switching control unit stops supply of a current from the power supply unit to the thermoelectric element when the temperature acquired by the first temperature measurement unit is determined to have reached the reference temperature during supply of the current from the power supply unit to the thermoelectric element.

12. The moisture sensor according to claim 5, wherein
the thermoelectric element includes a first heat input/output surface and a second heat input/output surface which are in contact with the measurement object and configured to provide heat to the measurement object and dissipate heat from the measurement object,
the temperature information acquisition unit includes a first temperature measurement unit attached to the first heat input/output surface, and a second temperature measurement unit attached to the second heat input/output surface on a side opposite to the first heat input/output surface,
the plurality of threshold values include one or more lower threshold values lower than the temperature of the measurement object before a start of measurement, and
the switching control unit switches a direction of the current when a temperature acquired by the first temperature measurement unit has reached the lower threshold value or when a temperature acquired by the second temperature measurement unit has reached the lower threshold value.

13. The moisture sensor according to claim 12, wherein the switching control unit stops supply of the current from the power supply unit to the thermoelectric element when the temperature acquired by the first temperature measurement unit and the temperature acquired by the second temperature measurement unit are determined to coincide with each other.

14. A moisture sensor which obtains moisture information on moisture contained in a measurement object, the moisture sensor comprising:
a thermoelectric element disposed in the measurement object and being able to change a temperature of the measurement object,
a power supply unit supplying a current to the thermoelectric element and being able to switch a direction of the current supplied to the thermoelectric element,
a temperature information acquisition unit acquiring the temperature of the measurement object; and
a moisture content acquisition unit controlling a direction of the current supplied to the thermoelectric element from the supply unit and acquiring the moisture information by utilizing the temperature acquired by the temperature information acquisition unit, wherein
the moisture content acquisition unit includes a switching control unit which controls a direction of the current supplied to the thermoelectric element from the power supply unit each time a predetermined switching time elapses, and
the moisture content acquisition unit acquires the moisture information by utilizing at least one extreme value of the temperature of the measurement object.

15. The moisture sensor according to claim 14, wherein
the thermoelectric element includes a first heat input/output surface and a second heat input/output surface which are in contact with the measurement object and configured to provide heat to the measurement object and dissipate heat from the measurement object,
the temperature information acquisition unit includes a first temperature measurement unit attached to the first heat input/output surface, and a second temperature measurement unit attached to the second heat input/output surface, and
the switching control unit stops supply of the current from the power supply unit to the thermoelectric element when a temperature acquired by the first temperature measurement unit and a temperature acquired by the second temperature measurement unit are determined to coincide with each other.

* * * * *